(12) United States Patent
Morita et al.

(10) Patent No.: US 8,500,822 B2
(45) Date of Patent: Aug. 6, 2013

(54) ARTIFICIAL TISSUE CONSTRUCT AND METHOD FOR PRODUCING THE SAME

(75) Inventors: Ikuo Morita, Tokyo (JP); Hideyuki Miyake, Tokyo (JP); Hideshi Hattori, Tokyo (JP); Hironori Kobayashi, Tokyo (JP); Yusuke Uno, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 1311 days.

(21) Appl. No.: 11/628,054

(22) PCT Filed: May 31, 2005

(86) PCT No.: PCT/JP2005/010307
§ 371 (c)(1),
(2), (4) Date: Nov. 30, 2006

(87) PCT Pub. No.: WO2005/118012
PCT Pub. Date: Dec. 15, 2005

(65) Prior Publication Data
US 2007/0259328 A1  Nov. 8, 2007

(30) Foreign Application Priority Data
Jun. 1, 2004  (JP) .................................. 2004-163512

(51) Int. Cl.
*A61F 2/02* (2006.01)
(52) U.S. Cl.
USPC ........ 623/23.72; 424/93.7; 435/395; 435/402
(58) Field of Classification Search
None
See application file for complete search history.

(56) References Cited

U.S. PATENT DOCUMENTS

| 7,759,113 B2 * | 7/2010 | Vacanti et al. ............. 435/284.1 |
| 2003/0109920 A1 * | 6/2003 | Martins-Green et al. .... 623/1.41 |

FOREIGN PATENT DOCUMENTS

| JP | 8-9960 A | 1/1996 |
| JP | 2002-542883 A | 12/2002 |
| JP | 2003-024351 A | 1/2003 |
| JP | 2003-038170 A | 2/2003 |
| JP | 2003-222626 A | 8/2003 |
| JP | 2005-000608 A | 1/2005 |
| WO | WO 99/52356 A1 | 10/1999 |
| WO | WO 02/08387 A1 | 1/2002 |
| WO | WO 2004/101774 A1 | 11/2004 |
| WO | WO 2005/038011 A1 | 4/2005 |

OTHER PUBLICATIONS

Francois Berthiaume, et al.; "Effect of Extracellular Matrix Topology on Cell Structure, Function, and Physiological Responsiveness: Hepatocytes Cultured in a Sandwich Configuration"; The FASEB Journal; Nov. 1996; vol. 10, No. 13; pp. 1471-1484.

A. Schneider, et al.; "An Improved Method of Endothelial Seeding on Small Caliber Prosthetic Vascular Grafts Coated with Natural Extracellular Matrix"; Clinical Materials; 1993; vol. 13, No. 1-4; pp. 51-55.

Nakayama, Yasuhide, "Free Design of Circuit of Capillary Network and Construction of Functional Hybrid Tissue", Research Promotion Achievement Report, Japan Cardiovascular Research Foundation, Dec. 2000, pp. 26-31.

M. Harimoto et al., "Novel approach for achieving double-lyered cell sheets co-culture: overlaying Endothelial cell sheets onto monolayer hepatocytes utilizing temperature-responsive culture dishes", J. Biomed. Mater. Res., 2002, p. 464-70, vol. 62, No. 3.

Masami Harimoto et al., "Ondo Otosei Baiyozara o Mochiita Kekkan Naihi Saibo to Kansaibo no Jusoka Kyobaiyo", Intelligent Zairyo Symposium Koen Yoshishu, 2002, p. 78-79, vol. 11.

\* cited by examiner

*Primary Examiner* — Allison Ford
(74) *Attorney, Agent, or Firm* — Sughrue Mion, PLLC

(57) ABSTRACT

An object of the present invention is to provide an artificial tissue construct that has means for transporting nutrients, oxygen, waste products, or the like and is viable in vivo. The present invention relates to a tissue construct formed in vitro, which comprises a vascular layer, a basal membrane layer, and a tissue-forming cell layer.

7 Claims, 11 Drawing Sheets
(3 of 11 Drawing Sheet(s) Filed in Color)

A

B

C

ARTIFICIAL TISSUE CONSTRUCT AND METHOD FOR PRODUCING THE SAME

TECHNICAL FIELD

The present invention relates to a tissue construct formed in vitro, which comprises a vascular layer, a basal membrane layer, and a tissue-forming cell layer, a laminated tissue construct comprising the tissue constructs, and a method for producing them.

BACKGROUND ART

Recently, technology for direct transplantation of artificial alternates or cell tissues obtained by culturing cells has been a focus of attention. Typical examples of such technology include artificial skin, artificial blood vessels, and cultured cell tissues. Artificial skin or the like containing a synthetic polymer is not preferable for transplantation because it may cause rejection or other problems. On the other hand, with a cultured cell tissue, there is no concern about rejection, because such tissue is obtained by culturing the cells of a subject into which the tissue will be transplanted and thus it is preferable for transplantation. Such cultured cell tissue is prepared by collecting cells from a subject for transplantation and then culturing the cells.

Many animal cells have adhesion dependency (cells grow while adhering to something). Animal cells are thus unable to survive for a long time period in a floating state ex vivo. In a cell culture for preparing the above cell tissue, for example, a polymer material such as modified polystyrene having enhanced cell adhesiveness through surface treatment or a culture plate that is prepared by uniformly applying a cell adhesive protein (e.g., collagen) or a cell-adhesive polymer (e.g., poly-L-lysine) to glass or a polymer material has been used as a carrier. Cells that have adhered to and grown on such carrier in a planar state grow under a culture environment while forming extracellular matrices comprising proteins and carbohydrates. In general, it is required to harvest such cultured cells through treatment with proteinase such as trypsin or a chemical drug. Thus, such process is problematic in that treatment steps become complicated, the possibility of contamination becomes high, cells are denatured or damaged, original cellular functions may deteriorate, and the like.

Accordingly, JP Patent Publication (Kokai) No. 2003-38170 A discloses a method for producing a cell sheet, which comprises preparing a cell culture support obtained by patterning a temperature-responsive polymer on a culture base, culturing cells on the cell culture support, causing the support to closely adhere to a polymer film by varying temperature, and removing the cells together with the polymer film from the support without damaging the cells, so as to produce a cell sheet.

However, transplantation or the like of such cell sheet obtained by the method disclosed herein into a living body is problematic in that an artificial tissue having a thickness of approximately several hundred microns prepared through multiple lamination of such multiple cell sheets lacks means for transporting nutrients, oxygen, and waste products, and thus it causes cell necrosis within the artificial tissue construct.

It is possible to form an artificial tissue construct with a thickness that does not cause cell necrosis within the tissue, followed by transplantation thereof into a living body, so as to cause angiogenesis to take place in vivo. However, such means is unrealistic, because few cells can be transplanted at a time by such means, and such transplantation should be carried out repeatedly to restore organ functions where there has been damage on a large scale.

Furthermore, a method for constructing an artificial organ using a specific cell culture method is also known (JP Patent Publication (Kokai) 2003-24351 A). With this method, an artificial blood vessel is formed by adhesion of vascular endothelial cells or the like to a tubular cell culture substrate. However, in order to prepare many artificial blood vessels by this method, many finely processed cell culture substrates must be prepared and tissue formation requires much time. Thus, such method has also low industrial productivity.

DISCLOSURE OF THE INVENTION

The present invention has been completed to address the above problems in the above conventional technology. Specifically, an object of the present invention is to provide an artificial tissue construct that has means for transporting nutrients, oxygen, waste products, or the like and is viable in vivo.

As a result of intensive studies to achieve the above object, the present inventors have discovered that an artificial tissue construct having blood vessel tissues can be produced by laminating together at least one layer of each of vascular, basal membrane, and tissue-forming cell layers. Thus, the present inventors have completed the present invention.

The present invention encompasses the following invention.

(1) A tissue construct formed in vitro, which comprises a vascular layer, a basal membrane layer, and a tissue-forming cell layer.

(2) The tissue construct according to (1), wherein the basal membrane layer is present on the tissue-forming cell layer and the vascular layer is present on the basal membrane layer.

(3) A laminated tissue construct formed in vitro, wherein vascular, basal membrane, and tissue-forming cell layers are laminated together and which comprises at least one layer of each of these 3 types of layers.

(4) The laminated tissue construct according to (3), wherein a basal membrane layer is present on a tissue-forming cell layer, a vascular layer is present on a basal membrane layer, and a tissue-forming cell layer is present on a basal membrane layer or a vascular layer.

(5) A method for producing a tissue construct comprising a tissue-forming cell layer, a basal membrane layer, and a vascular layer, which comprises the steps of:

(a) forming a tissue-forming cell layer on a culture base;

(b) forming a basal membrane layer on the obtained tissue-forming cell layer;

(c) causing angiogenic cells to adhere to regions having good cell adhesiveness on the surface of a cell array substrate having a cell adhesiveness variation pattern that comprises regions having good cell adhesiveness and regions having inhibited cell adhesiveness, transferring the adhered cells onto the basal membrane layer in such patterned state, and culturing the transferred cells; and (d) separating and collecting a tissue construct comprising the tissue-forming cell layer, the basal membrane layer, and the vascular layer from the culture base.

(6) A method for producing a laminated tissue construct, which comprises laminating together tissue constructs produced by the method according to (5).

(7) A method for producing a laminated tissue construct, which comprises producing a first tissue construct by a method comprising the following steps (a) to (d):
(a) forming a tissue-forming cell layer on a culture base;
(b) forming a basal membrane layer on the obtained tissue-forming cell layer;
(c) causing angiogenic cells to adhere to regions having good cell adhesiveness on the surface of a cell array substrate having a cell adhesiveness variation pattern that comprises regions having good cell adhesiveness and regions having inhibited cell adhesiveness, transferring the adhered cells onto the basal membrane layer in such patterned state, and culturing the transferred cells; and
(d) separating and collecting a first tissue construct comprising the tissue-forming cell layer, the basal membrane layer, and the vascular layer from the culture base, producing a second tissue construct by a method comprising the following steps (e) to (f):
(e) forming a tissue-forming cell layer on a culture base;
(f) forming a basal membrane layer on the obtained tissue-forming cell layer; and
(g) separating and collecting the tissue-forming cell layer and the basal membrane layer from the culture base, and laminating together the $1^{st}$ and the $2^{nd}$ tissue constructs.
(8) The method according to (6) or (7), which further comprises the step of transporting a culture solution to the vascular layer within the laminated tissue construct.
(9) The method according to any one of (5) to (8), wherein the cell adhesiveness variation layer is a photocatalyst-comprising cell adhesiveness variation layer that comprises a photocatalyst and the cell adhesiveness variation material.
(10) The method according to any one of (5) to (8), wherein the cell adhesiveness variation layer comprises a photocatalyst treatment layer that comprises a photocatalyst and a cell adhesiveness variation material layer that comprises the cell adhesiveness variation material formed on the photocatalyst treatment layer.
(11) The method according to (9), by which the cell adhesiveness variation pattern is formed by arranging the cell adhesiveness variation layer that comprises the cell adhesiveness variation material and the photocatalyst-comprising layer so that the layers face each other, and then carrying out energy irradiation.
(12) The method according to any one of (5) to (11), wherein the cell adhesiveness variation pattern is a pattern wherein linear regions having good cell adhesiveness and spaces comprised of the regions having inhibited cell adhesiveness are arranged alternately, the line widths of the regions having good cell adhesiveness are each between 20 μm and 200 μm, and the space widths between such lines are each between 100 μm and 1000 μm.
(13) The method according to any one of (5) to (12), wherein the culture base has a surface that is capable of retaining cells with weak adhesiveness.
(14) A method for regenerating a tissue, which comprises transplanting the tissue construct according to any one of (1) to (4).
(15) A tissue construct comprising a vascular layer, a basal membrane layer, and a tissue-forming cell layer, wherein the basal membrane layer is formed covering almost the entire surface of the vascular layer formation region of the tissue-forming cell layer.
(16) A laminated tissue construct, which comprises vascular, basal membrane, and tissue-forming cell layers and comprises at least one layer of each of these 3 types of layers, wherein a basal membrane layer is formed covering almost the entire surface of the vascular layer formation region of a tissue-forming cell layer.
(17) The laminated tissue construct according to (16), wherein a basal membrane layer is present on a tissue-forming cell layer, a vascular layer is present on a basal membrane layer, and a tissue-forming cell layer is present on a basal membrane layer or a vascular layer.

According to the present invention, an artificial tissue construct is provided, which has means for transporting nutrients, oxygen, waste products, or the like and is viable in vivo.

This description includes part or all of the contents as disclosed in the description and/or drawings of Japanese Patent Application No. 2004-163512, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

EXPLANATION OF SYMBOLS

Figure 1:
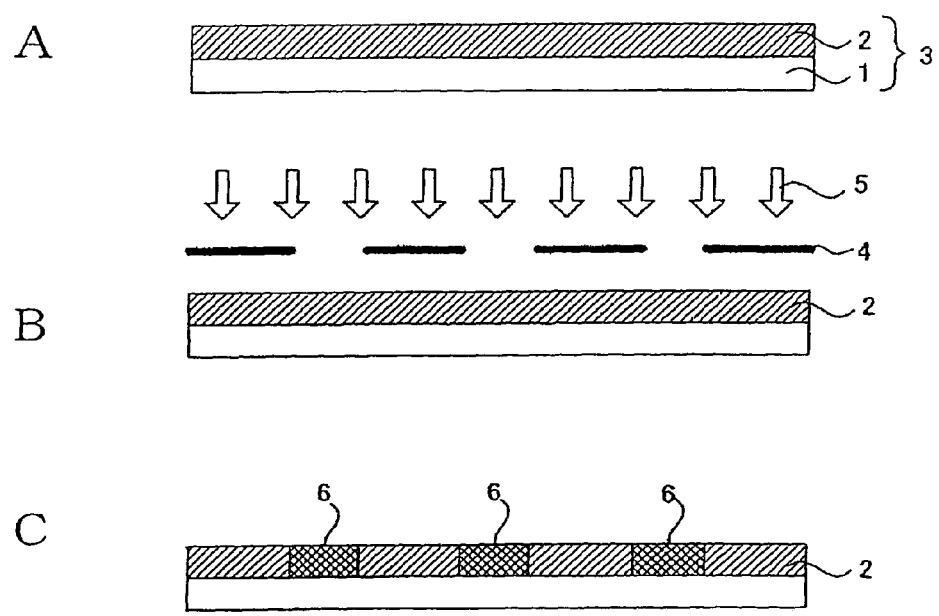
FIG. 1 shows an example of a step in the method for producing the cell array substrate of the present invention.

1: substrate, 2: photocatalyst-containing cell adhesiveness variation layer, 3: substrate for pattern formation, 4: photomask, 5: energy, 6: cell adhesiveness variation pattern, 15: cell array substrate, 16: basal membrane layer, 17: region having good cell adhesiveness, 18: region having inhibited cell adhesiveness, 19: cell, 20: water-repellent material, 21: cell-adhesive material, 22: cell stimulating factor, 101: tissue-forming cell, 102: culture base, 103: tissue-forming cell layer, 104: basal membrane layer, 105: cell array substrate, 106: angiogenic cells, 107: tissue construct, 108: vascular layer, 109: laminated tissue construct in which $1^{st}$ tissue constructs are laminated together, and 110: laminated tissue construct in which 1$^{st}$ and 2$^{nd}$ tissue constructs are laminated together The present invention will be described in detail below.

The present invention relates to a tissue construct formed in vitro, which comprises a vascular layer, a basal membrane layer, and a tissue-forming cell layer. "Vascular layer" means a layer containing angiogenic cells. Examples of angiogenic cells include vascular endothelial cells, smooth muscle cells, and mural cells. Vascular endothelial cells are preferable to avoid coagulation of blood components in blood vessels for smooth blood flow. Furthermore, angiogenic cells are desirably composed of vascular endothelial cells together with smooth muscle cells or mural cells in order to maintain functions and structures of the vascular endothelial cells. In the vascular layer, it is preferable that angiogenic cells be arrayed in a pattern. A pattern to be formed is not particularly limited, as long as it is a two-dimensional pattern. For example, a linear, a mesh, a circular, or a quadrille pattern, a pattern wherein the inside of each figure (e.g., circle or tetragram) is filled with cells, or the like can be formed. A linear or a mesh pattern is preferable. When angiogenic cells are arrayed in a linear or a mesh pattern and then cultured, tissue formation is promoted and angiogenesis is thus promoted. Hence, the vascular layer in the present invention preferably includes blood vessel tissue.

In the present invention, "basal membrane layer" means a layer that comprises a basal membrane constitutive protein as a major component. A "basal membrane layer" is an extracellular matrix in the form of a layer, which unites cell growth factors that stimulate cellular activity, a vascular layer, and a tissue-forming cell layer, so as to form an aggregate, and it contains collagen, fibronectin, and laminin. The basal membrane layer may be an extract from a living body or may be produced by cells. Furthermore, the basal membrane layer may also be formed with the addition of artificial substances.

"Tissue-forming cell layer" means a layer containing tissue-forming cells. "Tissue-forming cells" means cells having functions required for a tissue construct that is constituted in vitro. Examples of tissue-forming cells include organ cells. Specific examples of such organ cells include cells derived from organs of the metabolic system, such as hepatic parenchymal cells and pancreatic β cells, and cells derived from organs of the structural system, such as epithelial cells of the skin. In the above tissue construct, preferably, the basal membrane layer is present on the tissue-forming cell layer and the vascular layer is present on the basal membrane layer.

The present invention also relates to a laminated tissue construct, which is formed in vitro by laminating together vascular, basal membrane, and tissue-forming cell layers and comprises at least one layer of each of these 3 types of layers. In the laminated tissue construct, preferably, a basal membrane layer is present on a tissue-forming cell layer, a vascular layer is present on a basal membrane layer, and a tissue-forming cell layer is present on a basal membrane layer or a vascular layer. Specifically, the laminated tissue construct has a structure in which a three-layer structure and a two-layer structure are laminated together. In the three-layer structure, a basal membrane layer is present on a tissue-forming cell layer and a vascular layer is present on a basal membrane layer. In the two-layer structure, a basal membrane layer is present on a tissue-forming cell layer.

At least 1 and preferably 1 to 5 pieces of three-layer structures each having a vascular layer may be present in the laminated tissue construct. In the case of the two-layer structure wherein the basal membrane layer is present on the tissue-forming cell layer, generally 0 to 5 two-layer structures are present. Generally 5 to 10 structures are present in total, including two-layer and three-layer structures.

The above basal membrane layer is formed covering almost the entire surface of a region on the above tissue-forming cell layer on which a vascular layer is formed. "Almost the entire surface" means generally 90% or more and preferably 95% of the surface.

The present invention also relates to a method for producing in vitro a tissue construct comprising a vascular layer, a basal membrane layer, and a tissue-forming cell layer. The tissue construct can be produced by a method comprising the following steps (a) to (d):

(a) forming a tissue-forming cell layer on a culture base;
(b) forming a basal membrane layer on the obtained tissue-forming cell layer;
(c) causing angiogenic cells to adhere to regions having good cell adhesiveness on the surface of a cell array substrate having a cell adhesiveness variation pattern that comprises regions having good cell adhesiveness and regions having inhibited cell adhesiveness, transferring the adhered cells onto the basal membrane layer in such patterned state, and culturing the transferred cells; and
(d) separating and collecting a first tissue construct comprising the tissue-forming cell layer, the basal membrane layer, and the vascular layer from the culture base.

Figure 10:
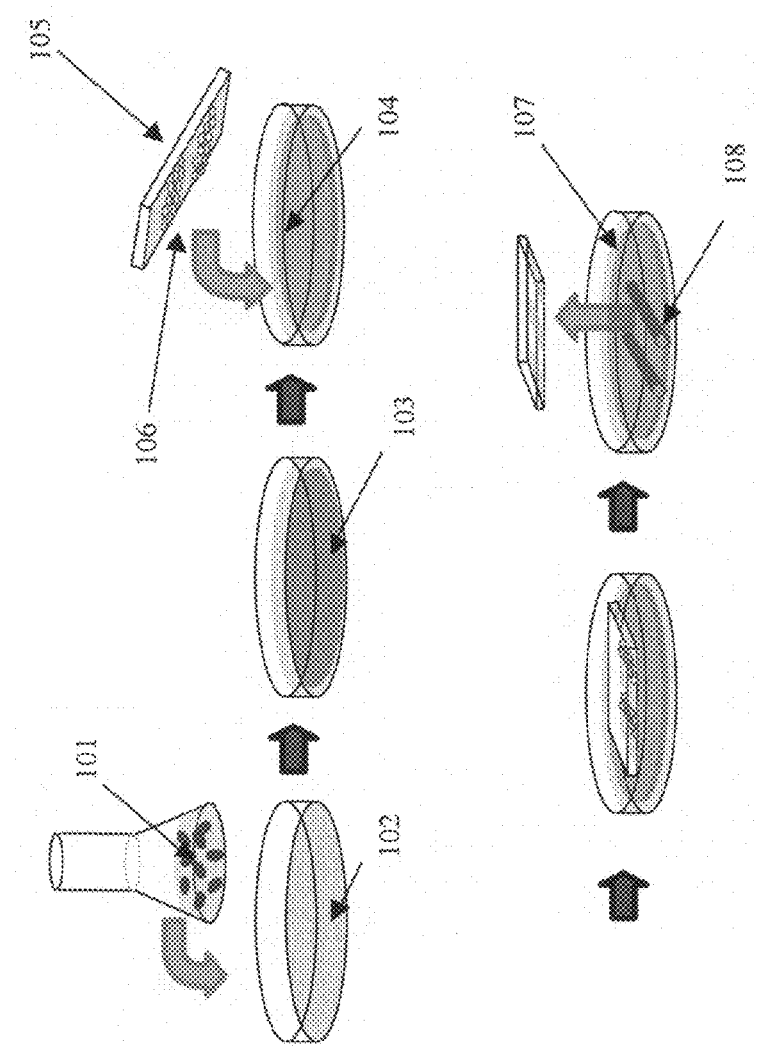
FIG. 10 shows an embodiment of a method for producing in vitro a tissue construct comprising a vascular layer, a basal membrane layer, and a tissue-forming cell layer.

FIG. 10 shows an embodiment of the above production method. In FIG. 10, 101 denotes tissue-forming cells, 102 denotes a culture base, 103 denotes a tissue-forming cell layer, 104 denotes a basal membrane layer, 105 denotes a cell array substrate, 106 denotes angiogenic cells, 107 denotes a formed tissue construct, and 108 denotes a vascular layer.

The culture base is not particularly limited, as long as a tissue-forming cell layer can be formed thereon. Preferably, a culture base from which a tissue construct can be separated without damaging such cell layer is used. Examples of such culture base include culture bases having surfaces capable of retaining cells with weak adhesiveness, such as a culture base prepared by subjecting a polystyrene substrate to weak plasma treatment for cell adhesion and a culture base prepared by introducing a small amount of a material such as 2-methacryloyloxyethyl phosphorylcholine or fluoroalkylsilane having property of inhibiting cell adhesion onto a substrate surface. Examples of such method for introducing a small amount of such material include a method that involves sufficiently introducing a material to a substrate through adsorption treatment or the like and then carrying out decomposition through UV treatment, ozone treatment, or plasma treatment and a method that involves coating with a solution in which a material is slightly dissolved to form a thin layer. The proportions of materials to be introduced differ and should be adjusted depending on cell types to be caused to adhere and material types to be introduced onto substrates.

Furthermore, there exist temperature-responsive polymer materials, such as poly-N-isopropylacrylamide. This material possesses hydrophobicity; that is, cell adhesiveness, under environment where the temperature is at a phase transition temperature or higher, but becomes hydrophilic at a phase transition temperature or lower so as to lose its cell adhesiveness. A cell base prepared by polymerizing such material on a polymer or a glass substrate is also an example. In the present invention, poly-N-isopropylacrylamide is preferably used.

The tissue-forming cell layer can be formed by a cell culture method that is generally employed in the technical field. For example, a tissue-forming cell layer can be formed by inoculating cells on a culture base at a density between $10^4$ and $10^8$ cells/cm$^2$ and then culturing the cells at 37° C. for 30 minutes to 48 hours. As a medium, a medium that is generally used in the technical field can be used. Examples of such a medium that can be used herein include an MEM medium, a BME medium, a DME medium, an (XMEM medium, an IMEM medium, an ES medium, a DM-160 medium, a Fisher medium, an F12 medium, a WE medium, an RPMI medium, any one of these media supplemented with a serum component (e.g., fetal calf serum), and a commercial serum-free medium.

The basal membrane layer can also be formed by culturing tissue-forming cells, or it may also be formed by adding a matrix. A matrix to be added herein is not particularly limited, as long as it contains collagen, laminin, or fibronectin. An example of such matrix is prepared by adding materials derived from a living body, such as collagen and laminin, to an artificial polymer material such as GFR Matrigel (e.g., Mebiol gel). In a case where a matrix is added, a basal membrane layer can be formed by carrying out incubation at approximately 37° C. for several hours after addition.

The vascular layer can be formed by causing the surface of a cell array substrate on which angiogenic cells are arrayed in a pattern to come into contact with the basal membrane layer, culturing the cells to form tissues, and then removing the cell array substrate. Culture conditions that are generally employed in the technical field can be employed. For example, culture may be carried out at 37° C. for generally 2 to 48 hours and preferably for 4 to 24 hours.

A cell array substrate having a cell adhesiveness variation pattern that comprises regions having good cell adhesiveness and regions having inhibited cell adhesiveness and adhesion of angiogenic cells to the regions having good cell adhesiveness on the surface are described later. Finally, the tissue construct comprising the tissue-forming cell layer, the basal membrane layer, and the vascular layer is separated and collected from the culture base.

The present invention further relates to a method for producing in vitro a laminated tissue construct in which vascular, basal membrane, and tissue-forming cell layers are laminated together. The thus produced laminated tissue construct comprises at least one layer of each of these 3 types of layers. The laminated tissue construct can be produced by producing $1^{st}$ tissue constructs each comprising a vascular layer, a basal membrane layer, and a tissue-forming cell layer, and then laminating together the thus produced $1^{st}$ tissue constructs. Alternatively, the laminated tissue construct can also be produced by producing the above $1^{st}$ tissue construct, producing a $2^{nd}$ tissue construct comprising a basal membrane layer and a tissue-forming cell layer by a method comprising the following steps (e) to (g):

(e) forming a tissue-forming cell layer on a culture base;
(f) forming a basal membrane layer on the obtained tissue-forming cell layer; and
(g) separating and collecting the tissue-forming cell layer and the basal membrane layer from the culture base; and then laminating together the $1^{st}$ and $2^{nd}$ tissue constructs.

Figure 11:
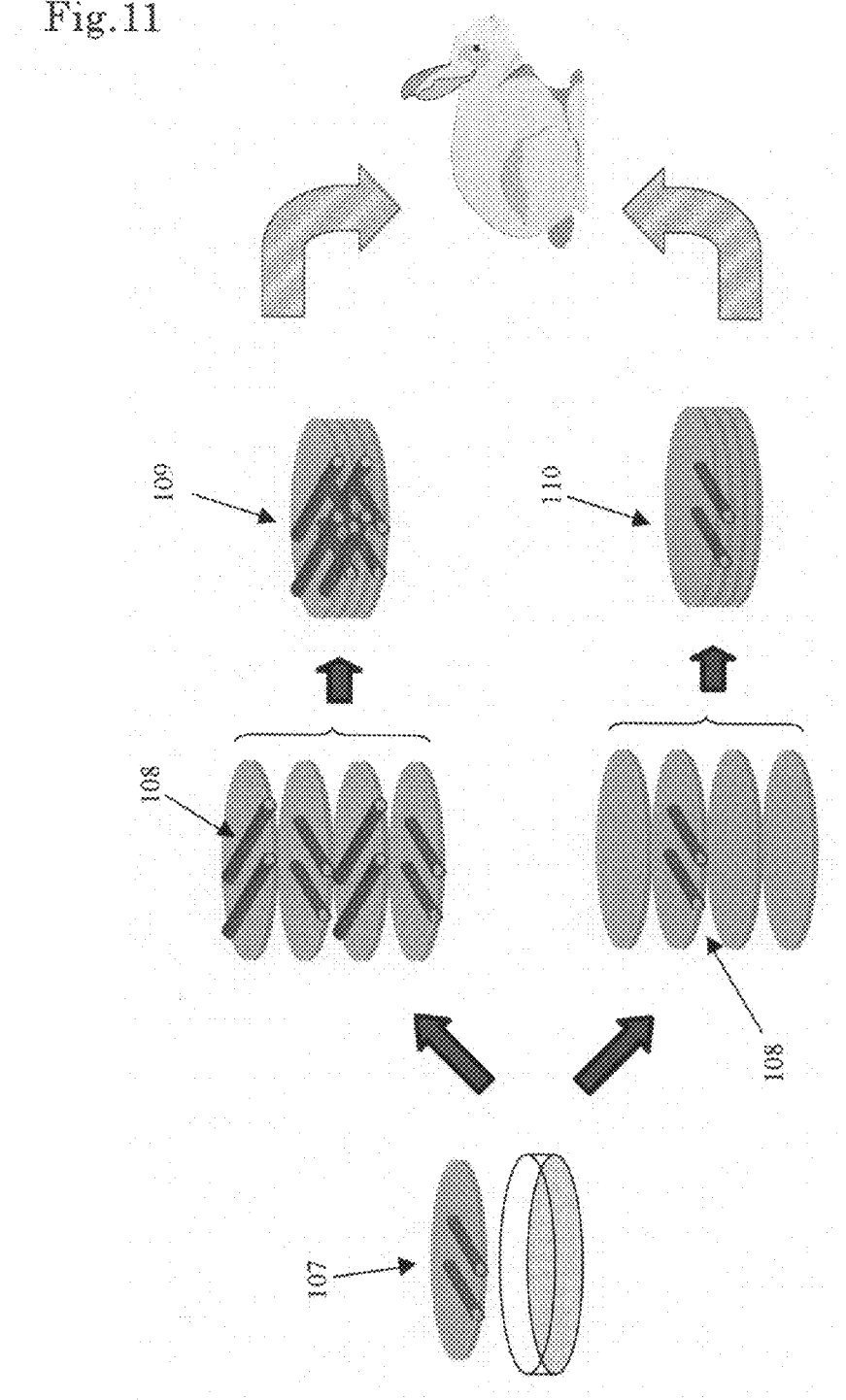
FIG. 11 shows an embodiment of a method for producing in vitro a laminated tissue construct in which vascular layers, basal membrane layers, and tissue-forming cell layers are laminated together.

FIG. 11 shows an embodiment of the above production method. In FIG. 11, 107 denotes a tissue construct, 108 denotes vascular layers, 109 denotes a laminated tissue construct produced by laminating $1^{st}$ tissue constructs, and 110 denotes a laminated tissue construct produced by laminating together the $1^{st}$ and $2^{nd}$ tissue constructs.

In the production of the $2^{nd}$ tissue construct, a culture base, a tissue-forming cell layer, and the basal membrane layer are formed in a manner similar to that in the production of the above $1^{st}$ tissue construct.

Here, the order of laminating together the $1^{st}$ and $2^{nd}$ tissue constructs is not particularly limited. 1 to 6 and preferably 2 to 3 pieces of $2^{nd}$ tissue constructs having no vascular layers are preferably present per 1 layer of the $1^{st}$ tissue construct.

After laminating such tissue constructs, preferably, a culture solution is transported to the vascular layers within the laminated tissue construct. This promotes the tissue formation by angiogenic cells arrayed in a pattern on each of the vascular layers.

I. Cell Array Substrate

The cell array substrate in the present invention is characterized in having a cell adhesiveness variation pattern that comprises regions having good cell adhesiveness and regions having inhibited cell adhesiveness patterned on a substrate.

"Cell adhesiveness" means strength for the adhesion of cells; that is, the degree of ease with which cells adhere. "Regions having good cell adhesiveness" means regions wherein cell adhesiveness is good. "Regions having inhibited cell adhesiveness" means regions wherein cell adhesiveness is poor. Accordingly, when cells are inoculated on such cell array substrate having a cell adhesiveness variation pattern, cells adhere to the regions having good cell adhesiveness, but no cells adhere to the regions having inhibited cell adhesiveness. Hence, cells are arrayed in a pattern on the surface of the cell array substrate.

Cell adhesiveness can differ depending on cells that are caused to adhere. Hence, "good cell adhesiveness" means that cell adhesiveness for a specific type of cell is good. Therefore, a plurality of regions having good cell adhesiveness are present corresponding to a plurality of types of cells on a cell array substrate. Specifically, regions having good cell adhesiveness, which vary in cell adhesiveness (2 or more different levels) may be present on the cell array substrate.

The cell adhesiveness variation pattern is, for example, formed by forming a cell adhesiveness variation layer that comprises a cell adhesiveness variation material whose cell adhesiveness is varied along with energy irradiation on a substrate, varying cell adhesiveness through energy irradiation on specific regions, and then forming a pattern wherein regions differ in cell adhesiveness. Examples of such material whose cell adhesiveness is varied include both a material whose cell adhesiveness is acquired or increased along with energy irradiation and a material whose cell adhesiveness is decreased or disappears along with energy irradiation.

A substrate used for the cell array substrate of the present invention is not particularly limited, as long as it is formed of a material capable of forming a cell adhesiveness variation pattern on its surface. Specific examples of such substrate include inorganic materials such as metal, glass, and silicon, and organic materials represented by plastic. The shape of such material is also not limited. Examples of such shape include a flat plate, a flat membrane, a film, and a porous membrane.

The cell adhesiveness variation material and the cell adhesiveness variation layer will be explained in an embodiment using a photocatalyst.

Another example included herein is a cell adhesiveness variation pattern that is formed of a cell-adhesion inhibiting layer that comprises a cell-adhesion-inhibiting material having low cell adhesiveness and a cell adhesion layer that is formed on the cell-adhesion-inhibiting layer and comprises a cell adhesive material having cell adhesiveness. Here, the cell adhesion layer is decomposed and then disappears along with energy irradiation to cause the cell-adhesion-inhibiting layer to be exposed, so that regions differing in cell adhesiveness are formed. Similarly, another example included herein is a cell adhesiveness variation pattern that is formed of a cell adhesion layer and a cell-adhesion-inhibiting layer formed on the cell adhesion layer, wherein the cell-adhesion-inhibiting layer is decomposed and then disappears along with energy irradiation to cause the cell adhesion layer to be exposed, so that regions differing in cell adhesiveness are formed.

Figure 8:
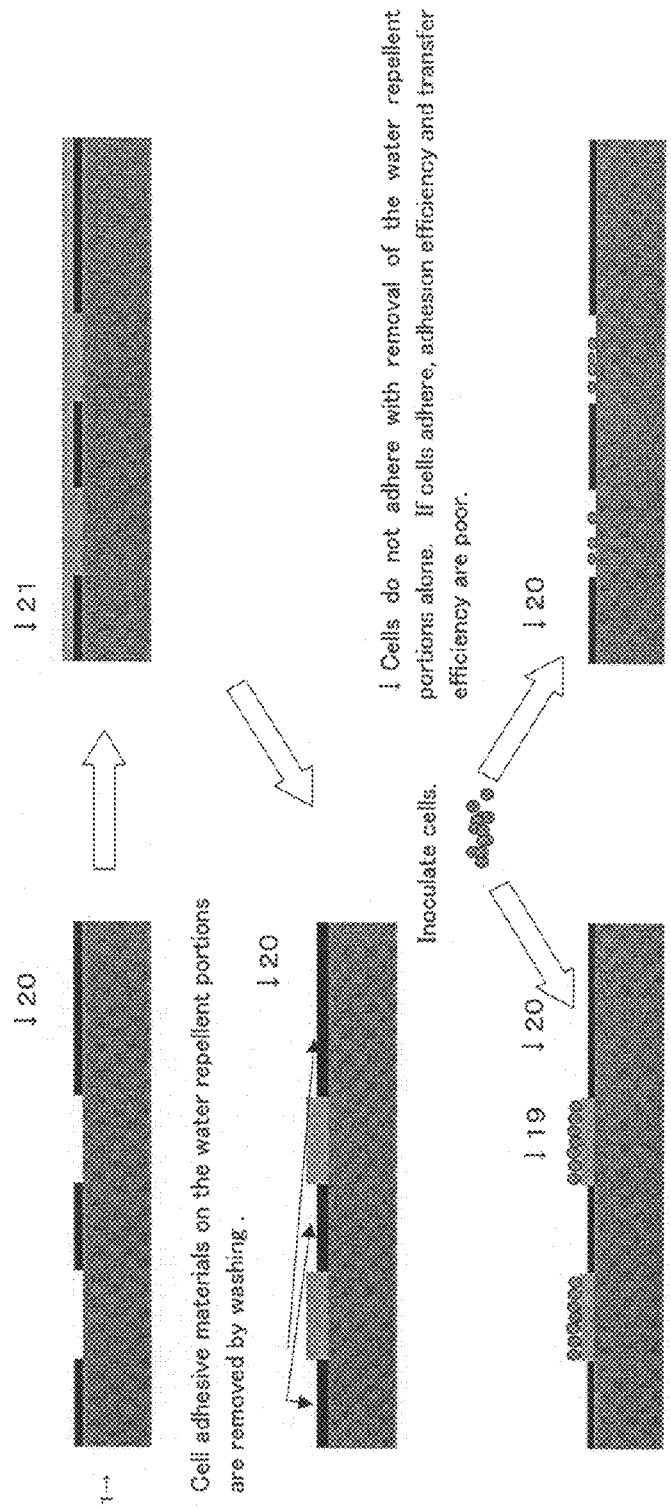
FIG. 8 is a schematic view showing an example of the method of the present invention.
Figure 9:
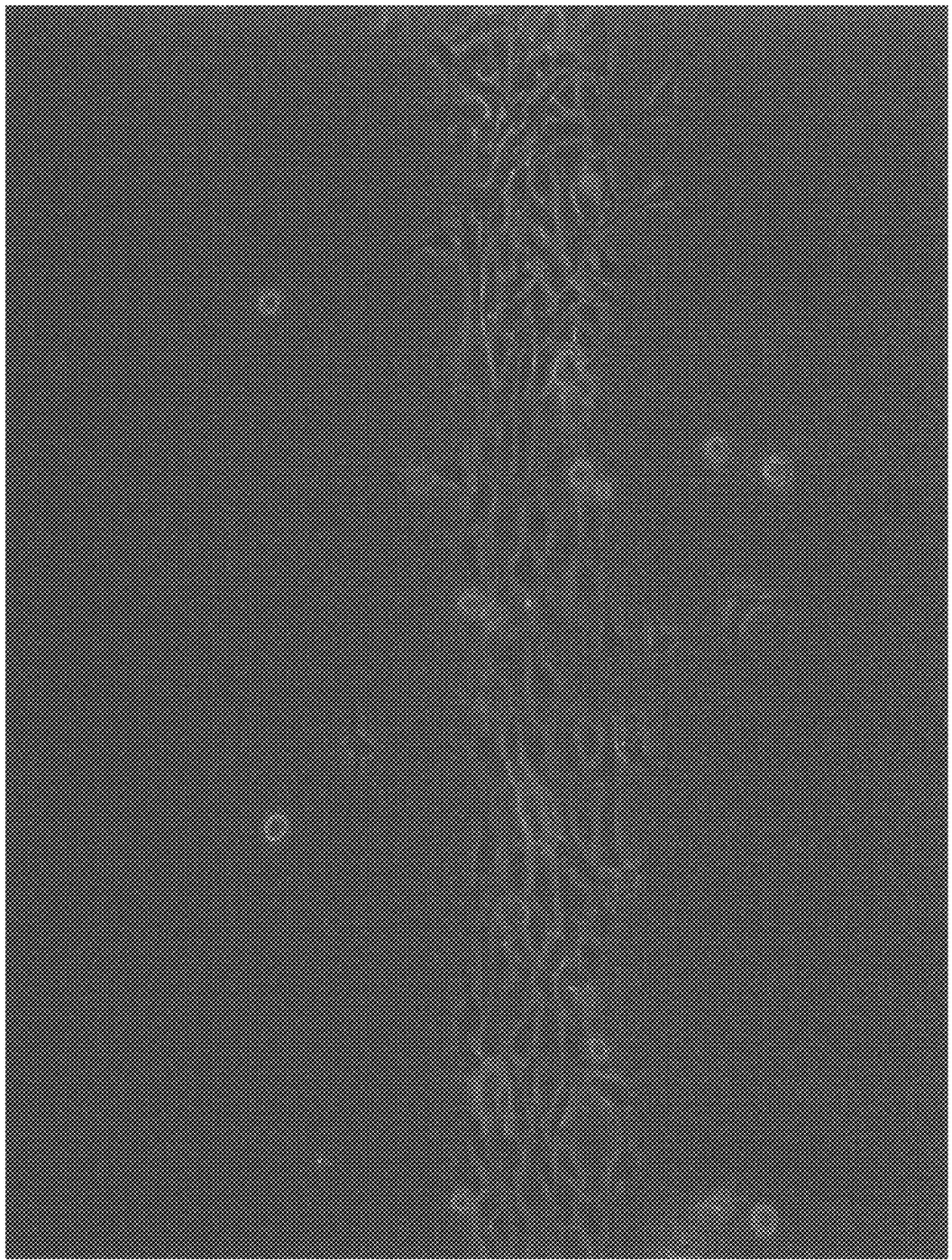
FIG. 9 is a photograph showing cells arrayed on a cell array substrate.

Examples of such cell adhesive material include extracellular matrices such as various types of collagen, fibronectin, laminin, vitronectin, and cadherin, and RGD peptide. Another example of the same is a polyolefin resin wherein a carbonyl group or a carboxyl group has been introduced by a technique such as plasma treatment, corona treatment, ion beam irradiation treatment, or electron beam irradiation treatment in order to impart cell adhesiveness. Examples of such cell-adhesion-inhibiting material include fluorine materials such as polytetrafluoroethylene (PTFE), polyimide, and phospholipid. Moreover, through the use of a method such as an inkjet method, a cell adhesive material may be put on a cell-adhesion-inhibiting layer to form a pattern or a cell-adhesion-inhibiting material may be put on a cell adhesion layer to form a pattern. Alternatively, a cell adhesiveness variation pattern that comprises regions where a cell adhesive material is present (regions having good cell adhesiveness) and regions where a cell adhesive material is absent (regions having inhibited cell adhesiveness) can also be formed by: forming a layer that comprises an affinity variation material whose affinity for a cell adhesive material is varied along with energy irradiation on a substrate; forming a pattern through energy irradiation that comprises regions having affinity for the cell adhesive material and regions lacking such affinity; introducing a solution that contains the cell adhesive material; and then washing. In such embodiment, a pattern can be formed using a cell adhesive material that cannot be directly patterned on a substrate. For example, as shown in FIG. 8, a pattern that comprises regions (20) comprising a layer that comprises a water repellent material and regions lacking such material is formed on a hydrophilic substrate (1) such as glass. A hydrophilic cell adhesive material (21) that is hardly adsorbed to the water repellent material is introduced thereto. The substrate is then washed. Accordingly, regions wherein the hydrophilic cell adhesive material is present (regions having good cell adhesiveness) and regions wherein the water repellent material is present (regions having inhibited cell adhesiveness) form a pattern. An extracellular matrix such as collagen can be used as such hydrophilic cell adhesive material to be used in this case.

In the present invention, cells arrayed in a pattern on a cell array substrate are transferred to a basal membrane layer. Hence, the cell adhesiveness of the above regions having good cell adhesiveness is preferably at a proper strength. With such proper adhesion strength, it becomes possible to easily transfer the cells to a basal membrane layer, while forming a cell pattern by adhering cells only to specific regions. Therefore, it is preferable that the cell adhesiveness of regions having good cell adhesiveness on a cell array substrate is higher than those of regions having inhibited cell adhesiveness, but lower than that of the basal membrane layer.

Such cell adhesiveness can be evaluated using a water contact angle on the surface. It is preferable that regions having good cell adhesiveness of the cell adhesiveness variation pattern in the present invention each have a water contact angle between 10° and 40°. When cells are caused to adhere to a cell array substrate and then transferred to a basal membrane layer with a water contact angle within such range, the cells can be caused to adhere to a cell array substrate in the form of a monolayer. And then, the cells can be easily transferred to a basal membrane layer because of weak adhesiveness to the cell array substrate. "Contact angle" means an angle formed by the surface of a liquid and the surface of a solid where the free surface of the liquid at rest comes into contact with the wall of the solid (angle measured within the liquid).

The term "water contact angle" used herein means a value measured using a static contact angle measurement method. The above water contact angle is generally observed by adding minute waterdrops dropwise to the surface of a material under atmospheric pressure using an instrument such as a syringe and then observing the angle formed by the liquid/vapor interface (at the droplet end) and the surface of a solid using a magnifying glass or the like.

There is no particular limitation of a means for forming the above cell adhesiveness variation pattern that comprises regions having good cell adhesiveness and regions having inhibited cell adhesiveness arranged in a pattern. Examples of such means include various printing methods such as a gravire printing method, a screen printing method, an offset printing method, a flexographic printing method, and a contact printing method, a method using various lithographic methods, a method based on an inkjet method, and three-dimensional modeling such as carving fine grooves. In the present invention, a lithographic method using a photocatalyst is preferable. Specifically, in such method, a cell adhesiveness variation material (whose cell adhesiveness is varied by the action of a photocatalyst along with energy irradiation) and the photocatalyst are used and energy irradiation that is carried out according to a required pattern, so as to form a required cell adhesiveness variation pattern. In such embodiment, a high-definition pattern can be formed with convenient steps without using any treatment solution that adversely affects cells. Moreover, such embodiment does not require any modification of a cell adhesiveness variation material. Thus, options for material selection can be expanded. Furthermore, a biological cell adhesiveness variation material that exerts specific adhesiveness described later can also be used without any problems.

A pattern to be formed is not particularly limited, as long as it is a two-dimensional pattern. Such pattern is designed according to the pattern of angiogenic cells, which is formed within a vascular layer in a tissue construct. Hence, it is preferable to form a pattern that enables cells to adhere in a linear or mesh pattern. When such linear or mesh pattern is formed, the line width in the pattern is generally between 20 μm and 200 μm and preferably between 50 μm and 100 μm. In particular, when capillary vessels are formed by arranging and culturing vascular endothelial cells in a line-shaped pattern, it is preferable that a cell adhesiveness variation pattern is formed where linear regions having good cell adhesiveness and spaces comprised of regions having inhibited cell adhesiveness are arranged alternately, so as to cause the vascular endothelial cells to adhere to form a linear pattern. In such embodiment, a pattern is preferably formed wherein cells are caused to adhere so that a line width can contain 1 to 10 cells and preferably 1 to 5 cells. Specifically, the line width of a region having good cell adhesiveness is generally between 20 μm and 200 μm, and preferably between 50 μm and 80 μm. The space widths between such lines (the spaces comprised of regions having inhibited cell adhesiveness) are each generally between 100 μm and 1000 μm and preferably between 400 μm and 800 μm. With a line width determined within the above numerical range, vascular endothelial cells can efficiently form a tubular tissue.

Through the formation of such cell adhesiveness variation pattern, vascular endothelial cells caused to adhere and then transferred in a linear pattern efficiently form a tissue; that is, a linear capillary vessel. When a cell pattern where a plurality of lines are arranged without crossing each other is formed, the space widths between the lines on which cells adhere are each set to be equal to or above a specific value as described above. Accordingly, the cells can be prevented from extending pseudopodia between the lines at the time of their tissue formation, which would distort the lines.

Examples of the above cell array substrate prepared by a lithographic method using a photocatalyst include the following three embodiments. Each of these embodiments will be described as follows.

A. 1st Embodiment

A 1st embodiment of the cell array substrate of the present invention is a cell array substrate comprising a cell adhesiveness variation layer that is formed on a substrate and comprises a cell adhesiveness variation material whose cell adhesiveness is varied by the action of a photocatalyst along with energy irradiation, wherein the above cell adhesiveness variation layer forms a cell adhesiveness variation pattern with variations in cell adhesiveness characterized in that the above cell adhesiveness variation layer is a photocatalyst-comprising cell adhesiveness variation layer that comprises the photocatalyst and the above cell adhesiveness variation material.

In this embodiment, the cell adhesiveness variation layer is a photocatalyst-comprising cell adhesiveness variation layer that comprises the photocatalyst and the above cell adhesiveness variation material. Thus, when energy irradiation is carried out, the cell adhesiveness of the cell adhesiveness variation material is varied by the action of the photocatalyst within the photocatalyst-comprising cell adhesiveness variation layer. Hence, a cell adhesiveness variation pattern that comprises portions subjected to energy irradiation and portions not subjected to energy irradiation, where the portions differ in terms of cell adhesiveness, can be formed.

Members used in such cell array substrate in this embodiment will be each described as follows.

1. Photocatalyst-Comprising Cell Adhesiveness Variation Layer

This embodiment is characterized in that a photocatalyst-comprising cell adhesiveness variation layer is formed on a substrate. The photocatalyst-comprising cell adhesiveness variation layer comprises at least a photocatalyst and a cell adhesiveness variation material.

(1) Cell Adhesiveness Variation Material

A cell adhesiveness variation material used in this embodiment is not particularly limited, as long as it is a material whose cell adhesiveness is varied by the action of a photocatalyst along with energy irradiation. Examples of such material whose cell adhesiveness is varied include both a material that acquires or increases its cell adhesiveness by the action of a photocatalyst along with energy irradiation and a material whose cell adhesiveness decreases or disappears due to the action of a photocatalyst along with energy irradiation.

There are two major embodiments of such cell adhesiveness variation material, which differ in an aspect to control cell adhesiveness. One embodiment is a physicochemical cell adhesiveness variation material that adheres to cells due to its physicochemical property and the other embodiment is a biological cell adhesiveness variation material that adheres to cells due to its biological property.

a. Physicochemical Cell Adhesiveness Variation Material

Examples of a physicochemical factor for causing cells to adhere to the surface include a factor relating to surface free energy, a factor relating to hydrophobic interaction, and the like.

A preferable physicochemical cell adhesive material having physicochemical cell adhesiveness due to the presence of such factor possesses binding energy that is sufficiently high so that the main backbone is not decomposed by the action of a photocatalyst and also has an organic substituent that is decomposed by the action of a photocatalyst. Examples of such material include (1) organopolysiloxane that is obtained through hydrolysis and polycondensation of such as chloro- or alkoxysilane using a sol-gel reaction or the like so as to exert high strength and (2) organopolysiloxane that is obtained through crosslinking of reactive silicones.

In the case of (1) above, a preferable organopolysiloxane is 1 or 2 or more types of hydrolysis condensate or cohydrolysis condensate of a silicon compound that is represented by general formula:

$$Y_n SiX_{(4-n)}$$

(where Y indicates an alkyl group, a fluoroalkyl group, a vinyl group, an amino group, a phenyl group, or an epoxy group; X indicates an alkoxyl group, an acetyl group, or halogen; and "n" is an integer between 0 and 3). In addition, the carbon number of a group indicated with Y is preferably within the range between 1 and 20. Furthermore, an alkoxy group indicated with X is preferably a methoxy group, an ethoxy group, a propoxy group, or a butoxy group.

Furthermore, polysiloxane comprising a fluoroalkyl group as an organic group can be particularly preferably used. Specific examples of such polysiloxane include hydrolysis condensate and cohydrolysis condensate of 1 or 2 or more types of the following fluoroalkyl silane. Such polysiloxane generally known as a fluorine silane coupling agent can be used. Examples are:

$CF_3(CF_2)_3CH_2CH_2Si(OCH_3)_3$;
$CF_3(CF_2)_5CH_2CH_2Si(OCH_3)_3$;
$CF_3(CF_2)_7CH_2CH_2Si(OCH_3)_3$;
$CF_3(CF_2)_9CH_2CH_2Si(OCH_3)_3$;
$(CF_3)_2CF(CF_2)_4CH_2CH_2Si(OCH_3)_3$;
$(CF_3)_2CF(CF_2)_6CH_2CH_2Si(OCH_3)_3$;
$(CF_3)_2CF(CF_2)_8CH_2CH_2Si(OCH_3)_3$;
$CF_3(C_6H_4)C_2H_4Si(OCH_3)_3$;
$CF_3(CF_2)_3(C_6H_4)C_2H_4Si(OCH_3)_3$;
$CF_3(CF_2)_5(C_6H_4)C_2H_4Si(OCH_3)_3$;
$CF_3(CF_2)_7(C_6H_4)C_2H_4Si(OCH_3)_3$;
$CF_3(CF_2)_3CH_2CH_2SiCH_3(OCH_3)_2$;
$CF_3(CF_2)_5CH_2CH_2SiCH_3(OCH_3)_2$;
$CF_3(CF_2)_7CH_2CH_2SiCH_3(OCH_3)_2$;
$CF_3(CF_2)_9CH_2CH_2SiCH_3(OCH_3)_2$;
$(CF_3)_2CF(CF_2)_4CH_2CH_2SiCH_3(OCH_3)_2$;
$(CF_3)_2CF(CF_2)_6CH_2CH_2SiCH_3(OCH_3)_2$;
$(CF_3)_2CF(CF_2)_8CH_2CH_2SiCH_3(OCH_3)_2$;
$CF_3(C_6H_4)C_2H_4SiCH_3(OCH_3)_2$;
$CF_3(CF_2)_3(C_6H_4)C_2H_4SiCH_3(OCH_3)_2$;
$CF_3(CF_2)_5(C_6H_4)C_2H_4SiCH_3(OCH_3)_2$;
$CF_3(CF_2)_7(C_6H_4)C_2H_4SiCH_3(OCH_3)_2$;
$CF_3(CF_2)_3CH_2CH_2Si(OCH_2CH_3)_3$;
$CF_3(CF_2)_5CH_2CH_2Si(OCH_2CH_3)_3$;
$CF_3(CF_2)_7CH_2CH_2Si(OCH_2CH_3)_3$;
$CF_3(CF_2)_9CH_2CH_2Si(OCH_2CH_3)_3$; and
$CF_3(CF_2)_7SO_2N(C_2H_5)C_2H_4CH_2Si(OCH_3)_3$.

Through the use of the above polysiloxane comprising a fluoroalkyl group as a physicochemical cell adhesive material, a portion not subjected to energy irradiation of a photocatalyst-comprising cell adhesiveness variation layer will form a surface lacking cell adhesiveness because of the presence of a portion having fluorine on the surface. On the other hand, a portion subjected to energy irradiation will form a surface having cell adhesiveness because of the removal of fluorine and the like and the resulting presence of a portion having an OH group and the like on the surface. Therefore, regions can be patterned so that portions subjected to energy irradiation and portions not subjected to energy irradiation differ in terms of cell adhesiveness.

Moreover, an example of reactive silicone in (2) above is a compound having a backbone that is represented by the following general formula.

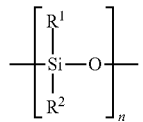

In the above formula, "n" is an integer of 2 or greater. $R^1$ and $R^2$ each indicate a $C_{1-10}$ substituted or unsubstituted alkyl, alkenyl, or aryl group. Examples of a substituent include halogen and cyano. Specific examples of $R^1$ and $R^2$ include methyl, ethyl, propyl, vinyl, phenyl, phenyl halide, cyano methyl, cyano ethyl, and cyano propyl. Vinyl, phenyl, or phenyl halide preferably constitutes 40% or less (in molar ratio) of the whole. Furthermore, a compound wherein $R^1$ and $R^2$ are each a methyl group is preferable because this results in the lowest surface energy. In addition, a methyl group constitutes preferably 60% (in molar ratio) or more of the whole. Furthermore, a chain terminus or a side chain has at least 1 or more reactive groups such as a hydroxyl group in a molecular chain.

Moreover, an organosilicone compound that does not undergo a crosslinking reaction and thus is stable, such as dimethyl polysiloxane, may also be separately mixed with the above organopolysiloxane.

Furthermore, an example of a physicochemical cell adhesive material (of a decomposable substance type) is a surfactant that is decomposed by the action of a photocatalyst and that has a function (exerted by decomposition) of varying the polarity of the surface of a photocatalyst-comprising polarity variation layer. Specific examples of such surfactant include hydrocarbon non-ionic surfactants (e.g., NIKKOL BL, BC, BO, and BB series produced by Nikko Chemicals Co., Ltd.) and fluorine or silicone non-ionic surfactants (e.g., ZONYL FSN and FSO produced by DuPont Kabushiki Kaisha, Surflon S-141 and 145 produced by ASAHI GLASS CO., LTD., Megafac F-141 and 144 produced by DAINIPPON INK AND CHEMICALS, INCORPORATED, FTERGENT F-200 and F251 produced by NEOS COMPANY LIMITED, Unidine DS-401 and 402 produced by DAIKIN INDUSTRIES, LTD., and Fluorad FC-170 and 176 produced by 3M (Minnesota Mining and Manufacturing Company). Moreover, a cationic surfactant, an anionic surfactant, or an amphoteric surfactant can also be used.

In addition, when a physicochemical cell adhesive material of a decomposable substance type is used as a material, generally preferably a binder component is separately used. Such binder component that is used in this case is not particularly limited, as long as it possesses binding energy that is sufficiently high so that the main backbone is not decomposed by the action of the above photocatalyst. Specific examples of such component include polysiloxane having no organic substituent and polysiloxane having little organic substituents. They can also be obtained by hydrolysis and polycondensation of tetramethoxysilane, tetraethoxysilane, or the like.

In addition, in this embodiment, a physicochemical cell adhesive material of such binder type and a physicochemical cell adhesive material of such decomposable substance type may be used together.

Another example is a physicochemical cell adhesiveness variation material whose cell adhesiveness is varied through the control of electrostatic interaction. In the case of such material, positively charged functional groups (contained in such material) are decomposed by the action of a photocatalyst along with energy irradiation. The amount of positive charge existing on the surface is then varied so as to vary adhesiveness between the surface and cells. Thus, a cell adhesiveness variation pattern is formed. An example of such material is poly L lysine.

b. Biological Cell Adhesiveness Variation Material

Examples of a biological factor for causing cells to adhere to the surface include a material that can have a property of adhering to many cell types and a material that has a property of adhering to only a specific cell type. The former material is a collagen I type material, for example. The latter material is poly(N-p-vinylbenzyl-[O-β-D-galactopyranosyl-(1→4)-D-gluconamide])(hereinafter, PVLA) that causes selective adhesion of hepatic parenchymal cells, for example. In the case of PVLA, it is inferred that selective and specific material-to-cell adhesion occurs, because PVLA has a galactose group that is specifically recognized by hepatic parenchymal cells in its structure.

When such material is mixed with a photocatalyst and then used for a photocatalyst-comprising cell adhesiveness variation layer, the following type of usage is possible. Collagen I type material is solubilized by enzyme treatment. The thus solubilized collagen I is mixed with a photocatalyst such as a $TiO_2$ particle that has been previously subjected to calcination treatment and grinding treatment, thereby preparing a material for a photocatalyst-comprising cell adhesiveness variation layer. Next, the material for the photocatalyst-comprising cell adhesiveness variation layer is applied to a substrate, thereby forming a photocatalyst-comprising cell adhesiveness variation layer When the photocatalyst-comprising cell adhesiveness variation layer is irradiated with a small amount of energy, a cell adhesive peptide structure in a side chain of collagen is partially disrupted. Thus, cell adhesiveness can be decreased. Furthermore, such cell adhesive peptide structure can be gradually caused to disappear by increasing the amount of energy irradiation. Furthermore, cell adhesiveness can be further decreased.

Furthermore, an excessive amount of energy irradiation can lead to disruption of the main chain structure of collagen and complete loss of the cell adhesiveness.

(2) Photocatalyst

Examples of a photocatalyst that is used in this embodiment include those known as optical semiconductors such as titanium dioxide ($TiO_2$), zinc oxide (ZnO), tin oxide ($SnO_2$), strontium titanate ($SrTiO_3$), tungsten oxide ($WO_3$), bismuth oxide ($Bi_2O_3$), and iron oxide ($Fe_2O_3$). 1 or 2 or more types of optical semiconductor can be selected from the above examples, mixed, and then used.

In this embodiment, titanium dioxide is particularly preferably used because it possesses high band gap energy, is chemically stable, is free from toxicity, and can be easily obtained. There exist anatase-type and rutile-type titanium dioxide, and both can be used in this embodiment. The anatase-type titanium dioxide is preferable. The anatase type titanium dioxide has an excitation wavelength of 380 nm or less.

Examples of such anatase-type titanium dioxide include anatase-type titaniasol of hydrochloric acid deflocculation type (STS-02 (average particle size of 7 nm) produced by ISHIHARA SANGYO KAISHA, LTD. and ST-K01 produced by ISHIHARA SANGYO KAISHA, LTD.) and anatase-type titaniasol of nitric acid deflocculation type (TA-15

(average particle size of 12 nm) produced by NISSAN CHEMICAL INDUSTRIES, LTD.).

A smaller photocatalyst particle size is preferable, because photocatalyst reactions take place more effectively with smaller particle size. The average particle diameter is preferably 50 nm or less. It is particularly preferable to use a photocatalyst with an average diameter of 20 nm or less.

The content of a photocatalyst in a photocatalyst-comprising cell adhesiveness variation layer that is used in this embodiment can be determined to be within a range between 5 wt. % and 60 wt. %, and preferably between 20 wt. % and 40 wt. %.

2. Substrate

A substrate that is used as the cell array substrate of the present invention is not particularly limited, as long as it is formed of a material with which a photocatalyst-comprising cell adhesiveness variation layer can be formed on the surface. Any form can be selected for such substrate, as long as surface treatment can be carried out through exposure treatment. Specific examples of such material include inorganic materials such as metal, glass, and silicon and organic materials represented by plastic. The shape of such substrate is also not limited. Examples of such shape include a flat plate, a flat membrane, a film, and a porous membrane.

3. Cell Adhesiveness Variation Pattern

In this embodiment, the above-described photocatalyst-comprising cell adhesiveness variation layer is formed on the above substrate, and then the substrate is subjected to energy irradiation in a pattern. Thus, a cell adhesiveness variation pattern with variation in cell adhesiveness is formed.

Such cell adhesiveness variation pattern is generally formed of regions having good cell adhesiveness (with good cell adhesiveness) and regions having inhibited cell adhesiveness (with poor cell adhesiveness). Through adhesion of cells to the regions having good cell adhesiveness, the cells can be adhered in a high-definition pattern. Such regions having good cell adhesiveness and such regions having inhibited cell adhesiveness are determined depending on the type of a cell adhesiveness variation material that is used herein.

For example, a cell adhesiveness variation material may be a physicochemical cell adhesiveness variation material that causes variation in cell adhesiveness by varying the surface free energy. In such case, the surface free energy that is within a predetermined range tends to result in good cell adhesiveness, but the surface free energy that is out of such range tends to result in decreased cell adhesiveness. A known example of variation in cell adhesiveness due to surface free energy is provided by the experimental results shown in the lower part of page 109, Frontiers of Biomaterials, under the general editorship of Yoshihito Ikada, CMC Publishing CO., LTD.

Cell adhesiveness can also be determined depending not only on the surface free energy of the above material, but also on the combination of a cell type and a material type that are caused to come into contact.

Here, such cell adhesiveness variation pattern is a pattern comprising the above regions having good cell adhesiveness and the above regions having inhibited cell adhesiveness. Depending on its application, it may be a cell adhesiveness variation pattern comprising regions where surface cell adhesiveness is varied by at least 3 different levels.

This is because, in a case where a photocatalyst-comprising cell adhesiveness variation layer comprising a biological cell adhesiveness variation material is used or in a case where it has not yet been confirmed if cell adhesiveness is good, or the like, it may be advantageous in terms of ability of finding optimum states for adhesiveness by successively causing changes to the surface states of a photocatalyst-comprising cell adhesiveness variation layer.

As described above, in the present invention, 3 or more different levels of cell adhesiveness include a state where cell adhesiveness is successively varied. The appropriate level of cell adhesiveness is appropriately selected depending on each circumstance and then determined.

Regions having such multiple different levels of adhesiveness can be formed by varying the amount of energy irradiation to a photocatalyst-comprising cell adhesiveness variation layer. Specific examples of such method include a method using half-tone photomasks varying in transmittance and a method that involves performing overlap exposure more than once using a plurality of photomasks differing from each other in shielding portion pattern.

Furthermore, a cell adhesiveness variation pattern that can be used in this embodiment uses a difference in photocatalyst activity between a portion subjected to energy irradiation and a portion not subjected to energy irradiation. Specifically, for example, a biological cell adhesiveness variation material that has been introduced as a decomposable substance into a photocatalyst-comprising cell adhesiveness variation layer is used. When the surface of such photocatalyst-comprising cell adhesiveness variation layer is irradiated with energy in a pattern, the biological cell adhesiveness variation material that has exuded on the surface of the irradiated portion is decomposed and the biological cell adhesiveness variation material of the unirradiated portion remains. Hence, when such biological cell adhesiveness variation material has good adhesiveness to a specific cell type or has good adhesiveness to many cell types, such unirradiated portions become to be regions having good cell adhesiveness. The irradiated portions become to be regions where a biological cell adhesiveness variation material having good adhesiveness to a cell is absent. Furthermore, the irradiated portions also become to be regions where a photocatalyst having activated sterility has been exposed as a result of energy irradiation. Therefore, when an energy-irradiated portion results in regions having inhibited cell adhesiveness, particularly when culture is carried out using the cell array substrate in this embodiment for a predetermined time period, such regions are advantageous in terms of not causing problems such as a wider pattern width.

B. $2^{nd}$ Embodiment

A $2^{nd}$ embodiment of the cell array substrate of the present invention is a cell array substrate comprising a substrate and a cell adhesiveness variation layer that is formed on the substrate and comprises a cell adhesiveness variation material whose cell adhesiveness is varied by the action of a photocatalyst along with energy irradiation, wherein the above cell adhesiveness variation layer forms a cell adhesiveness variation pattern with variation in cell adhesiveness characterized in that: the above cell adhesiveness variation layer comprises a photocatalyst-comprising photocatalyst treatment layer and a cell adhesiveness variation material layer that is formed on the above photocatalyst treatment layer and comprises the above cell adhesiveness variation material.

In this embodiment, such cell adhesiveness variation layer comprises a photocatalyst treatment layer formed on a substrate and a cell adhesiveness variation material layer formed on the photocatalyst treatment layer. Thus, when energy irradiation is carried out, the cell adhesiveness of the cell adhesiveness variation material within the cell adhesiveness variation material layer is varied by the action of the photocatalyst within the photocatalyst treatment layer. Hence, a cell adhesiveness variation pattern comprising portions subjected to energy irradiation and portions not subjected to energy irradiation, where the portions differ in terms of cell adhesiveness, can be formed.

Members used in such cell array substrate in this embodiment will be separately described as follows.

1. Cell Adhesiveness Variation Material Layer

In the cell array substrate of this embodiment, a cell adhesiveness variation material layer is formed on a photocatalyst treatment layer that is formed on the substrate. As such cell adhesiveness variation material layer, a layer that is formed with the use of a cell adhesiveness variation material explained in the above $1^{st}$ embodiment can be used. A cell adhesiveness variation material layer prepared with the use of a physicochemical cell adhesiveness variation material and a cell adhesiveness variation material layer prepared with the use of a biological cell adhesiveness variation material will be separately explained as follows.

(1) Use of Physicochemical Cell Adhesiveness Variation Material

In this embodiment, a cell adhesiveness variation material layer formed of a physicochemical cell adhesiveness variation material may be prepared as a layer prepared with the use of a material similar to that explained in the above $1^{st}$ embodiment. When such material is used, the thus prepared layer is similar to the above layer except for the presence or the absence of a photocatalyst. In addition, in this embodiment, a cell adhesiveness variation material layer is not principally required to comprise a photocatalyst therewithin, but may comprise a photocatalyst in a small amount in view of sensitivity or the like.

Furthermore, in this embodiment, a cell adhesiveness variation material layer is formed as a layer to be decomposed and removed (that is, the layer is decomposed and removed by the action of a photocatalyst) on a photocatalyst treatment layer. Regions wherein the cell adhesiveness variation material layer has been decomposed by the action of the photocatalyst along with energy irradiation (that is, regions wherein the photocatalyst treatment layer has been exposed) and regions wherein the cell adhesiveness variation material layer has remained are then formed. Thus, a cell adhesiveness variation pattern is formed. Such type of cell adhesiveness variation material layer having the thus formed pattern can be used.

Specifically, when cell adhesiveness is controlled with surface free energy, a physicochemical cell adhesiveness variation material whose surface free energy is appropriate for cell adhesiveness is used. Such material is applied to the whole surface, thereby forming a cell adhesiveness variation material layer. Subsequently, patterned energy irradiation is carried out according to a pattern, so as to form a pattern comprising regions of presence of and of absence of the cell adhesiveness variation material layer. Thus, a cell adhesiveness variation pattern is formed.

Examples of such physicochemical cell adhesiveness variation material layer that is used as a layer to be decomposed and removed and can be used for controlling cell adhesiveness with surface free energy include regenerated cellulose and nylon 11.

Furthermore, when cell adhesiveness is controlled with electrostatic interaction, a cell adhesiveness variation pattern can be formed using a positively charged physicochemical cell adhesiveness variation material and by a method similar to the above method.

Examples of a material that is used for such physicochemical cell adhesiveness variation material layer used as a layer to be decomposed and removed and can be used for controlling cell adhesiveness with electrostatic interaction include polyamine graft poly(2-hydroxymethylmethacrylate)(HA-x) and the like.

These resins are dissolved in a solvent and a film can be formed by a general film production method such as a spin coat method. Moreover, in the present invention, a defect-free film can be formed with the use of a functional thin film such as a self-organizing monomolecular film, Langmuir-Blodgett film, or an alternate adsorption film. Thus, it is preferable to use such film production method.

When a cell adhesiveness variation pattern is formed using a cell adhesiveness variation material layer as such layer to be decomposed and removed, regions subjected to decomposition and removal are regions within which cell culture is greatly inhibited, because in such regions a photocatalyst treatment layer is exposed. Hence, a cell array substrate that is obtained by such method is advantageous in that it can maintain a high-definition pattern even after keeping cells for a long time.

(2) Use of Biological Cell Adhesiveness Variation Material

In this embodiment, a material similar to that explained in the $1^{st}$ embodiment can be used for a cell adhesiveness variation material layer that is formed of a biological cell adhesiveness variation material. An example of such material is collagen I type.

2. Photocatalyst Treatment Layer

Next, a photocatalyst treatment layer that is used in the present invention will be explained. Such photocatalyst treatment layer used in the present invention is not particularly limited, as long as it is constituted in such a manner that the cell adhesiveness of a cell adhesiveness variation material layer (which is formed on a photocatalyst treatment layer) is varied by a photocatalyst in the photocatalyst treatment layer. Such photocatalyst treatment layer may be a layer composed of a photocatalyst and a binder or a layer prepared by a film production method using a photocatalyst alone. Furthermore, the surface may particularly be lyophilic or lyophobic. A lyophilic surface is preferable in terms of convenience of forming a cell adhesiveness variation material layer and the like on the photocatalyst treatment layer.

In such photocatalyst treatment layer, the action mechanism of a photocatalyst represented by titanium oxide that is described later is not always clear. It is thought that a direct reaction between a carrier generated by light irradiation and a neighboring compound or active oxygen species generated in the presence of oxygen and water causes a change in the chemical structure of organic matters. In the present invention, it is considered that such carrier acts on a compound in a cell adhesiveness variation material layer formed on a photocatalyst treatment layer. Examples of such photocatalyst are similar to those described in detail in the $1^{st}$ embodiment.

The photocatalyst treatment layer in this embodiment may be a layer formed of a photocatalyst alone as described above or a layer formed by mixing it with a binder.

A photocatalyst treatment layer consisting of a photocatalyst alone is advantageous in terms of cost, because its efficiency of causing variation in the cell adhesiveness of a cell adhesiveness variation material layer is improved and a treatment time is reduced. On the other hand, a photocatalyst treatment layer consisting of a photocatalyst and a binder is advantageous in that a photocatalyst treatment layer can be easily formed.

Examples of a method for forming a photocatalyst treatment layer consisting of a photocatalyst alone include a sputtering method, a CVD method, and a vacuum film production method such as a vacuum deposition method. Formation of a photocatalyst treatment layer by the vacuum film production method enables preparation of a photocatalyst treatment layer formed of a uniform film and comprising a photocatalyst alone. Thus, the properties of a cell adhesiveness variation material layer can be uniformly varied. Furthermore, since such layer consists of a photocatalyst alone, it becomes possible to vary the cell adhesiveness of a cell adhesiveness variation layer more efficiently than in the case of using a binder.

Moreover, another example of a method for forming a photocatalyst treatment layer consisting of a photocatalyst alone is, when a photocatalyst is titanium dioxide, a method that comprises forming amorphous titania on a substrate and then causing a phase change through calcination to obtain crystalline titania. Amorphous titania that is used herein can be obtained by hydrolysis or dehydration and condensation of inorganic salts of titanium, such as titanium tetrachloride and titanium sulfate, or hydrolysis, or dehydration and condensation of an organic titanium compound, such as tetraethoxy titanium, tetraisopropoxy titanium, tetra-n-propoxy titanium, tetrabutoxy titanium, and tetramethoxy titanium in the presence of acid. Subsequently, such titania is modified to result in anatase-type titania through calcination at a temperature between 400 C.° and 500° C. or to result in rutile-type titania through calcination at a temperature between 600° C. and 700° C.

Furthermore, when a binder is used, a preferable binder possesses binding energy that is sufficiently high so that the main backbone of the binder is not decomposed by the action of the above photocatalyst. Examples of such binder include the above organopolysiloxane and the like.

When organopolysiloxane is used as a binder as described above, the above photocatalyst treatment layer can be formed by dispersing a photocatalyst and organopolysiloxane that is the binder in a solvent together with another additive, if necessary, preparing an application solution, and then applying the application solution to a transparent substrate. A solvent that is used herein is preferably an alcohol-based organic solvent such as ethanol or isopropanol. Application can be carried out by a known application method such as a spin coating, a spray coating, a dip coating, a roll coating, or a bead coating method. When a UV-hardened type component is contained as a binder, a photocatalyst treatment layer can be formed through UV irradiation to carry out hardening treatment.

Furthermore, an amorphous silica precursor can be used as a binder. As such amorphous silica precursor, a silicon compound represented by general formula $SiX_4$, wherein X is halogen, a methoxy group, an ethoxy group, an acetyl group, or the like, silanol that is a hydrolysate thereof, or polysiloxane with an average molecular weight of 3000 or less is preferable.

Specific examples of such precursor include tetraethoxysilane, tetraisopropoxy silane, tetra-n-propoxy silane, tetrabutoxy silane, and tetramethoxysilane. Furthermore, in this case, a photocatalyst treatment layer can be formed by uniformly dispersing an amorphous silica precursor and photocatalyst particles in a non-aqueous solvent, subjecting the resultant to hydrolysis on a transparent substrate by water in air, so as to form silanol, and then carrying out dehydration, condensation, and polymerization at normal temperature. A process of dehydration, condensation, and polymerization of silanol at 100° C. or higher results in an increased polymerization degree of silanol and thus can improve the strength of the film surface. Moreover, such binding agent can be used alone, or a mixture of 2 or more types of such binding agents can be used.

The content of a photocatalyst in a photocatalyst treatment layer when a binder is used can be determined within a range between 5 wt. % and 60 wt. %, and preferably between 20 wt. % and 40 wt. %. Furthermore, the thickness of a photocatalyst treatment layer is preferably within a range between 0.05 μm and 10 μm.

Furthermore, a photocatalyst treatment layer may comprise a surfactant in addition to the above photocatalyst and binder. Specific examples of such surfactant include hydrocarbon non-ionic surfactants (e.g., NIKKOL BL, BC, BO, and BB series produced by Nikko Chemicals Co., Ltd.), fluorine or silicone non-ionic surfactants (e.g., ZONYL FSN and FSO produced by DuPont Kabushiki Kaisha, Surflon S-141 and 145 produced by ASAHI GLASS CO., LTD., Megafac F-141 and 144 produced by DAINIPPON INK AND CHEMICALS, INCORPORATED, FTERGENT F-200 and F251 produced by NEOS COMPANY LIMITED, Unidine DS-401 and 402 produced by DAIKIN INDUSTRIES, LTD., and Fluorad FC-170 and 176 produced by 3M (Minnesota Mining and Manufacturing Company). Moreover, a cationic surfactant, an anionic surfactant, or an amphoteric surfactant can also be used.

Furthermore, a photocatalyst treatment layer can comprise, in addition to the above surfactant, an oligomer, a polymer, or the like such as polyvinyl alcohol, unsaturated polyester, acrylic resin, polyethylene, diallyl phthalate, ethylene propylene diene monomer, epoxy resin, phenol resin, polyurethane, melamine resin, polycarbonate, poly(vinyl chloride), polyamide, polyimide, styrene butadiene rubber, chloroprene-rubber, polypropylene, polybutylene, polystyrene, poly(vinyl acetate), polyester, polybudadiene, polybenzimidazole, polyacryl nitrile, epichlorohydrin, polysulfide, and polyisoprene.

3. Substrate

A substrate that is used in this embodiment is not particularly limited, as long as the above photocatalyst treatment layer can be formed. A substrate similar to that explained in the $1^{st}$ embodiment can be used.

4. Cell Adhesiveness Variation Pattern

In this embodiment, a cell adhesiveness variation pattern is formed, wherein the cell adhesiveness of the surface of a cell adhesiveness variation material layer is varied by the action of a photocatalyst in a photocatalyst treatment layer as a result of energy irradiation carried out in a pattern on the above cell adhesiveness variation material layer.

C. Third Embodiment

A cell array substrate in this embodiment comprises a substrate and a cell adhesiveness variation layer that is formed on the above substrate and comprises a cell adhesiveness variation material whose cell adhesiveness is varied by the action of a photocatalyst along with energy irradiation, wherein the above cell adhesiveness variation layer forms a cell adhesiveness variation pattern with variation in cell adhesiveness, characterized in that: the above cell adhesiveness variation layer is a cell adhesiveness variation material layer comprising the above cell adhesiveness variation material; and the above adhesiveness variation pattern is formed by arranging a photocatalyst-comprising layer and the above cell adhesiveness variation material layer so that the layers face each other, and then carrying out energy irradiation from a predetermined direction.

In this embodiment, a cell adhesiveness variation layer is a cell adhesiveness variation material layer as described above; and the above adhesiveness variation pattern is formed by arranging a photocatalyst-comprising layer and the above cell adhesiveness variation material layer so that the layers face each other, and then carrying out energy irradiation from a predetermined direction. Thus, at the time of energy irradiation, the cell adhesiveness of the cell adhesiveness variation material within the cell adhesiveness variation material layer is varied by the action of the photocatalyst within the photocatalyst-comprising layer. Hence, such cell adhesiveness variation pattern can be formed, comprising portions subjected to energy irradiation and portions not subjected to energy irradiation, where such portions differ in terms of cell adhesiveness.

Members used in such cell array substrate in this embodiment will be separately explained.

1. Cell Adhesiveness Variation Material Layer

In the case of a cell array substrate of this embodiment, a cell adhesiveness variation material layer is formed on the substrate. Such cell adhesiveness variation material layer is similar to a layer that is formed with the use of a material explained in the above $2^{nd}$ embodiment. In addition, in this embodiment, a cell adhesiveness variation material layer is not principally required to comprise a photocatalyst therewithin, but may comprise a photocatalyst in a small amount in view of sensitivity and the like.

Furthermore, in this embodiment, in a manner similar to that in the above $2^{nd}$ embodiment, a cell adhesiveness variation material layer may be formed as a layer to be decomposed and removed (that is, the layer is subjected to decomposition and removal through the action of a photocatalyst) on a substrate. In this case, energy irradiation is carried out using a photocatalyst-comprising-layer-side base plate, so as to form regions wherein the cell adhesiveness variation material layer has been decomposed by the action of the photocatalyst along with energy irradiation (that is, the regions where the substrate has been exposed) and regions where the cell adhesiveness variation material layer has remained. Thus, a cell adhesiveness variation pattern is formed. Such type of cell adhesiveness variation material layer having the thus formed pattern is used.

2. Substrate

A substrate that is used in this embodiment is not particularly limited, as long as the above cell adhesiveness variation material layer can be formed. A substrate similar to that explained in the $1^{st}$ embodiment can be used.

3. Photocatalyst-Comprising Layer

Next, a photocatalyst-comprising layer that is used in this embodiment will be explained as follows. Such photocatalyst-comprising layer that is used in this embodiment is a layer comprising a photocatalyst. Such layer is generally formed on a base body such as glass and then used. In this embodiment, such photocatalyst-comprising layer is arranged so that the layer and the above cell adhesiveness variation material layer face each other. Through energy irradiation, the cell adhesiveness of the cell adhesiveness variation material layer can be varied by the action of the photocatalyst contained in such photocatalyst-comprising layer. In this embodiment, such photocatalyst-comprising layer is arranged at a predetermined position when energy irradiation is carried out, so that a cell adhesiveness variation pattern can be formed. Thus, there is no need to cause the above cell adhesiveness variation material layer to comprise a photocatalyst. Hence, such photocatalyst-comprising layer is advantageous in that a cell adhesiveness variation material layer can be kept free from the action of a photocatalyst over time.

Such photocatalyst-comprising layer is similar to the photocatalyst treatment layer that is explained in the above $2^{nd}$ embodiment.

4. Cell Adhesiveness Variation Pattern

In this embodiment, a cell adhesiveness variation pattern is formed in the above cell adhesiveness variation material layer. Such cell adhesiveness variation pattern is formed by carrying out energy irradiation in a pattern using the above photocatalyst-comprising layer, so as to vary the cell adhesiveness of the surface of the cell adhesiveness variation material layer by the action of the photocatalyst in the photocatalyst-comprising layer.

II. Method for Producing a Cell Array Substrate

Next, the method for producing a cell array substrate of the present invention will be explained. Examples of such method for producing the cell array substrate of the present invention include three embodiments as described above. All of these embodiments are characterized by the formation of a substrate for pattern formation that comprises a substrate and a layer formed on the substrate, whose adhesiveness can be varied by the action of a photocatalyst along with energy irradiation, irradiating energy to the substrate for pattern formation, so as to cause the photocatalyst to act thereon, followed by the formation of a cell adhesiveness variation pattern with variation in cell adhesiveness.

According to the method for producing the cell array substrate of the present invention, a layer whose cell adhesiveness is varied by the action of a photocatalyst along with the above energy irradiation is formed. Thus, through energy irradiation in a required pattern, it becomes possible to easily produce a cell array substrate on which a cell adhesiveness variation pattern (with variation in cell adhesiveness in a high-definition pattern) is formed. Therefore, a cell array substrate with a high-definition pattern can be produced with convenient steps without using any treatment solution that adversely affects cells. Moreover, such production method does not require any modification of a cell adhesiveness variation material. Thus, options for material selection can be expanded. Furthermore, a biological cell adhesiveness variation material that exerts specific adhesiveness described later can also be used without any problems.

The above $1^{st}$ to $3^{rd}$ embodiments for the method for producing a cell array substrate of the present invention will be separately explained as follows.

A. $1^{st}$ Embodiment

First, the $1^{st}$ embodiment of the cell array substrate of the present invention will be explained. The $1^{st}$ embodiment of the method for producing a cell array substrate of the present invention comprises: a step of forming a substrate for pattern formation that comprises a substrate and a photocatalyst-comprising cell adhesiveness variation layer formed on the above substrate and comprising a photocatalyst and a cell adhesiveness variation material whose cell adhesiveness is varied by the action of the photocatalyst along with energy irradiation; and a step of forming a cell adhesiveness variation pattern by irradiating energy to the above photocatalyst-comprising cell adhesiveness variation layer so as to vary the cell adhesiveness of the above photocatalyst-comprising cell adhesiveness variation layer.

A method for producing a cell array substrate in this embodiment is carried out as shown in FIG. 1, for example. Specifically, a substrate for pattern formation 3 (the step of forming a substrate for pattern formation (FIG. 1(a)) comprising a substrate 1 and a photocatalyst-comprising cell adhesiveness variation layer 2 formed on the substrate 1 is formed. Next, the step of forming a cell adhesiveness variation pattern (FIG. 1(c)) is carried out by irradiating the above photocatalyst-comprising cell adhesiveness variation layer 2 with energy 5 using a photomask 4, for example (FIG. 1(b)), and then forming a cell adhesiveness variation pattern 6 wherein the cell adhesiveness of a photocatalyst-comprising cell adhesiveness variation layer 2 has been varied.

In this embodiment, a photocatalyst-comprising cell adhesiveness variation layer comprising a photocatalyst and the above cell adhesiveness variation material is formed. Through energy irradiation in the step of forming a cell adhesiveness variation pattern, the cell adhesiveness of the cell adhesiveness variation material is varied by the action of the photocatalyst within the photocatalyst-comprising cell adhesiveness variation layer. Thus a cell adhesiveness variation pattern comprising portions subjected to energy irradiation and portions not subjected to energy irradiation, where the portions differ in terms of cell adhesiveness, can be formed. Each step of this embodiment will be explained.

1. Step of Forming a Substrate for Pattern Formation

First, the step of forming a substrate for pattern formation in this embodiment will be explained. The step of forming a substrate for pattern formation in this embodiment is a step for forming such substrate that comprises a substrate and a photocatalyst-comprising cell adhesiveness variation layer that is formed on the substrate and comprises a photocatalyst and a cell adhesiveness variation material whose cell adhesiveness is varied by the action of the photocatalyst along with energy irradiation.

This step can be carried out by applying a coating solution comprising a photocatalyst and a cell adhesiveness variation material to a substrate by a known application method such as a spin coating, a spray coating, a dip coating, a roll coating, or a bead coating method and thus forming a photocatalyst-comprising cell adhesiveness variation layer. When a UV-hardened type component is contained as a binder, a photocatalyst-comprising layer can be formed through UV irradiation to carry out hardening treatment.

2. Step of Forming a Cell Adhesiveness Variation Pattern

Next, the step of forming a cell adhesiveness variation pattern in this embodiment will be explained. The step of forming a cell adhesiveness variation pattern in this embodiment is a step for forming such pattern by subjecting the above photocatalyst-comprising cell adhesiveness variation layer to energy irradiation and thus forming a cell adhesiveness variation pattern wherein the cell adhesiveness of the above photocatalyst-comprising cell adhesiveness variation layer has been varied.

With this step, wherein energy irradiation is carried out in a desired pattern, the cell adhesiveness of only the regions (of a photocatalyst-comprising cell adhesiveness variation layer) subjected to energy irradiation can be varied. Furthermore, a high-definition cell adhesiveness variation pattern comprising regions having good cell adhesiveness and regions having poor cell adhesiveness can be formed.

"Energy irradiation (exposure)" used in this embodiment is a concept that includes any form of irradiation with energy rays capable of causing variation in the cell adhesiveness on the surface of a photocatalyst-comprising cell adhesiveness variation layer. Such energy irradiation is not limited to irradiation with visible light.

Light wavelength that is used for such energy irradiation is generally determined to be 400 nm or less and preferably 380 nm or less. This is because a preferable photocatalyst that is used for a photocatalyst-comprising cell adhesiveness variation layer as described above is titanium dioxide and light having a wavelength as described above is preferable as energy to activate the action of a photocatalyst with the use of such titanium dioxide.

Examples of a light source that can be used for such energy irradiation include a mercury lamp, a metal halide lamp, a xenon lamp, an excimer lamp, and other various light sources.

In addition to a method that comprises carrying out patterned irradiation via a photomask using the above light source, a method that comprises carrying out irradiation so as to draw a pattern using a laser such as excimer or YAG can also be used.

The amount of energy irradiation should be the amount of irradiation required for varying the cell adhesiveness of the surface of a photocatalyst-comprising cell adhesiveness variation layer by the action of the photocatalyst within such layer.

The cell adhesiveness of the surface of a photocatalyst-comprising cell adhesiveness variation layer is varied depending on the amount of energy irradiation. Hence, the adhesiveness can be adjusted by regulating the energy irradiation time, for example. Therefore, the surface can be prepared to have proper adhesiveness. Cell adhesiveness can be evaluated using the water contact angle on the surface as described above. Through regulation of the energy irradiation time to obtain a surface having a proper water contact angle, a surface having a proper adhesiveness can be prepared. For example, when fluoroalkyl silane is used as a cell adhesiveness variation material and the material is irradiated with ultraviolet light at 365 nm and at an intensity of 25.0 mW/second, and then quartz is used for the substrate of a photomask, a surface having preferable adhesiveness can be prepared through generally 120 to 600 seconds and preferably 240 to 480 seconds of irradiation. Such energy irradiation time, irradiation intensity, and the like can be appropriately regulated depending on a material for a substrate, a cell adhesiveness variation material, and the like to be used herein.

At this time, it is preferable to carry out energy irradiation while heating a photocatalyst-comprising cell adhesiveness variation layer. This is preferable because sensitivity can be elevated and cell adhesiveness can be varied efficiently. Specifically, heating within a range between 30° C. and 80° C. is preferable.

Regarding direction for energy irradiation in this embodiment, when the above substrate is transparent, patterned energy irradiation or laser irradiation to draw a pattern can also be carried out via a photomask from either the substrate side or the photocatalyst-comprising cell adhesiveness variation layer side. On the other hand, when a substrate is opaque, energy irradiation should be carried out from the photocatalyst-comprising cell adhesiveness variation layer side.

B. $2^{nd}$ Embodiment

Next, the $2^{nd}$ embodiment of the method for producing a cell array substrate of the present invention will be explained. The $2^{nd}$ embodiment of the cell array substrate of the present invention comprises: a step of forming a substrate for pattern formation that comprises a substrate, a photocatalyst-comprising photocatalyst treatment layer formed on the above substrate, and a cell adhesiveness variation material layer being formed on the above photocatalyst treatment layer and comprising a cell adhesiveness variation material whose cell adhesiveness is varied by the action of the photocatalyst along with energy irradiation; and a step of forming a cell adhesiveness variation pattern by subjecting the above cell adhesiveness variation material layer to energy irradiation so as to vary the cell adhesiveness of the above cell adhesiveness variation material layer.

Figure 2:
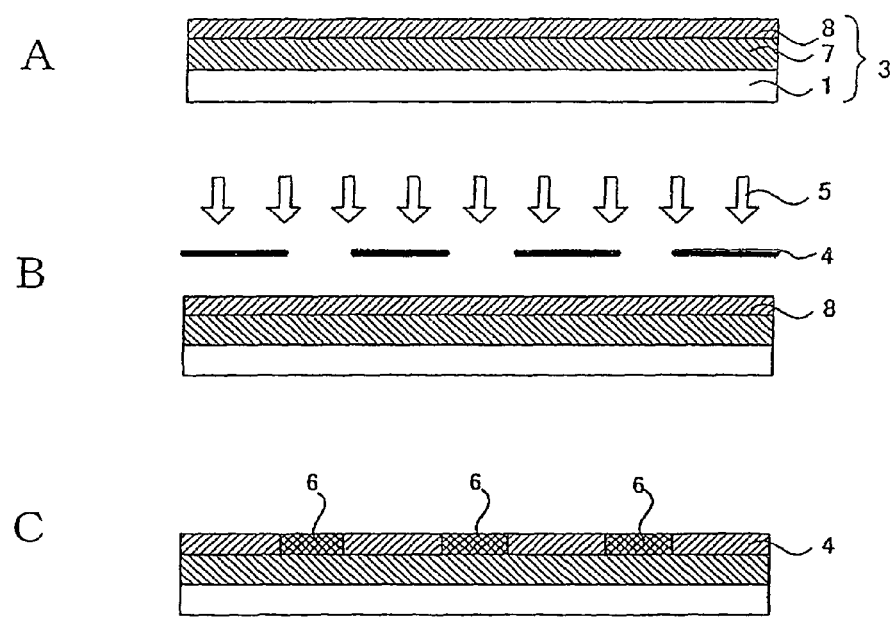
FIG. 2 shows another example of a step in the method for producing the cell array substrate of the present invention.

The method for producing a cell array substrate in this embodiment is carried out as shown in FIG. 2, for example. Specifically, a substrate for pattern formation 3 (the step of forming a substrate for pattern formation (FIG. 2(a)) comprising a substrate 1, a photocatalyst treatment layer 7 that is formed on the substrate 1, and a cell adhesiveness variation material layer 8 that is formed on the photocatalyst treatment layer 7 is formed. Next, the step of forming a cell adhesiveness variation pattern (FIG. 2(c)) is carried out by irradiating the above cell adhesiveness variation material layer 8 with energy 5 using a photomask 4, for example (FIG. 2(b)), and then forming a cell adhesiveness variation pattern 6 wherein the cell adhesiveness of the cell adhesiveness variation material layer 8 has been varied.

In this embodiment, a photocatalyst treatment layer and the above cell adhesiveness variation material layer are formed. Through energy irradiation in the step of forming a cell adhesiveness variation pattern, the cell adhesiveness within the cell adhesiveness variation material layer is varied by the action of the photocatalyst contained in the photocatalyst treatment layer. Thus, a cell adhesiveness variation pattern comprising portions subjected to energy irradiation and portions not subjected to energy irradiation, where the portions differ in terms of cell adhesiveness, can be formed. Each step of this embodiment will be explained as follows.

1. Step of Forming a Substrate for Pattern Formation

First, the step of forming a substrate for pattern formation in this embodiment will be explained. The step of forming a substrate for pattern formation in this embodiment is a step for forming such substrate that comprises a photocatalyst-comprising photocatalyst treatment layer formed on the above substrate and a cell adhesiveness variation material layer that is formed on the above photocatalyst treatment layer and comprises a cell adhesiveness variation material whose cell adhesiveness is varied by the action of the photocatalyst along with energy irradiation.

Such photocatalyst treatment layer that is formed in this step may consist of a photocatalyst alone or may be formed by mixture with a binder.

Examples of a method for forming a photocatalyst treatment layer consisting of a photocatalyst alone include a sputtering method, a CVD method, and a vacuum film production method such as a vacuum deposition method. For example, a method that is used when a photocatalyst is titanium dioxide comprises forming amorphous titania on a substrate and then causing a phase change through calcination to obtain crystalline titania. Formation of a photocatalyst treatment layer by the vacuum film production method enables preparation of a photocatalyst treatment layer formed of a uniform film and comprising a photocatalyst alone. Thus, the cell adhesiveness on a cell adhesiveness variation material layer can be uniformly varied. Furthermore, such layer consists of a photocatalyst alone. Thus, it becomes possible to vary the cell adhesiveness on a cell adhesiveness variation material layer more efficiently than in the case of using a binder.

Furthermore, when a photocatalyst treatment layer is prepared by mixing a photocatalyst with a binder, such layer can be formed by preparing an application solution by dispersing such photocatalyst and such binder in a solvent together with another additive if necessary and then applying the thus prepared application solution to a transparent substrate. A solvent that is used herein is preferably an alcohol-based organic solvent such as ethanol or isopropanol. Application can be carried out by a known application method such as a spin coating, a spray coating, a dip coating, a roll coating, or a bead coating method. When a UV-hardened type component is contained as a binder, a photocatalyst treatment layer can be formed through UV irradiation to carry out hardening treatment.

Subsequently, a coating solution comprising the above cell adhesiveness variation material is applied onto the above photocatalyst treatment layer by a known application method such as a spin coating, a spray coating, a dip coating, a roll coating, or a bead coating method. Thus, a cell adhesiveness variation material layer can be formed. When a UV-hardened type component is contained as a binder, a photocatalyst treatment layer can be formed through UV irradiation to carry out hardening treatment.

Such substrate, such photocatalyst treatment layer, and such cell adhesiveness variation material layer that are used in this step are similar to those explained in the above section of the $2^{nd}$ embodiment, "I. Cell array substrate."

2. Step of Forming a Cell Adhesiveness Variation Pattern

Next, the step of forming a cell adhesiveness variation pattern in this embodiment will be explained. The step of forming a cell adhesiveness variation pattern in this embodiment is a step for forming such pattern by subjecting the above cell adhesiveness variation material layer to energy irradiation and thus forming a cell adhesiveness variation pattern wherein the cell adhesiveness of the above cell adhesiveness variation material layer has been varied.

With this step wherein energy irradiation is carried out in a desired pattern, the cell adhesiveness of regions (of a cell adhesiveness variation material layer) subjected to energy irradiation can be exclusively varied. Furthermore, a high-definition cell adhesiveness variation pattern can be formed, which comprises regions having good cell adhesiveness and regions having poor cell adhesiveness.

An energy irradiation method, energy to be used for irradiation, and the amount of energy irradiation that are used in this step are similar to those in the above $1^{st}$ embodiment.

C. $3^{rd}$ Embodiment

Next, the $3^{rd}$ embodiment of the cell array substrate of the present invention will be explained. The $3^{rd}$ embodiment of the method for producing a cell array substrate of the present invention comprises: a step of forming a substrate for pattern formation that comprises a substrate and a cell adhesiveness variation material layer that is formed on the substrate and comprises a cell adhesiveness variation material whose cell adhesiveness is varied by the action of a photocatalyst along with energy irradiation; and a step of forming a cell adhesiveness variation pattern by arranging the above substrate for pattern formation and a photocatalyst-comprising-layer-side base plate that comprises a photocatalyst-comprising layer and a base body so that the above cell adhesiveness variation material layer and the above photocatalyst-comprising layer face each other, carrying out energy irradiation from a predetermined direction, and thus forming a cell adhesiveness variation pattern wherein the cell adhesiveness of the above cell adhesiveness variation material layer has been varied.

Figure 3:
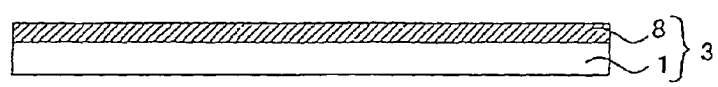
FIG. 3 shows another example of a step in the method for producing the cell array substrate of the present invention.
Figure 3:
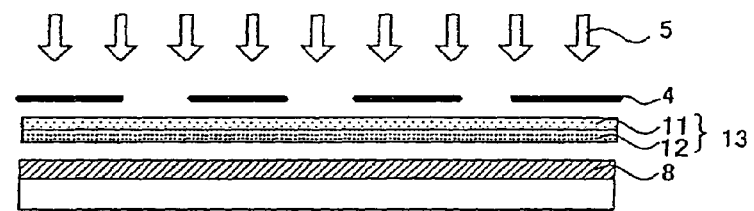
Figure 3:
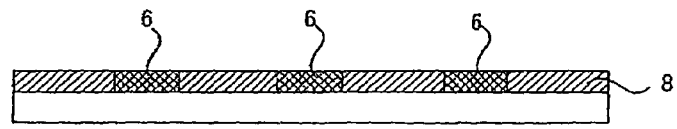

The method for producing a cell array substrate in this embodiment is carried out as shown in FIG. 3, for example. Specifically, a substrate for pattern formation 3 is formed (the step of forming a substrate for pattern formation (FIG. 3(a)), which comprises a substrate 1 and a cell adhesiveness variation material layer 8 formed on the substrate 1. Next, a photocatalyst-comprising-layer-side base plate 13 is prepared, which comprises a base body 11 and a photocatalyst-comprising layer 12 formed on the base body 11. The step of forming a cell adhesiveness variation pattern is carried out (FIG. 3(c)) by arranging the photocatalyst-comprising layer 12 in the photocatalyst-comprising-layer-side base plate 13 and the above cell adhesiveness variation material layer 8 so that the layers face each other, irradiating with energy 5 using a photomask 4, for example (FIG. 3(b)), and then forming a cell adhesiveness variation pattern 6 wherein the cell adhesiveness of the cell adhesiveness variation material layer 8 has been varied.

In this embodiment, the above cell adhesiveness variation material layer is formed. Through energy irradiation using the photocatalyst-comprising layer-side base plate in the step of forming a cell adhesiveness variation pattern, the cell adhesiveness within the cell adhesiveness variation material layer is varied by the action of the photocatalyst contained in the photocatalyst-comprising layer. Thus a cell adhesiveness variation pattern can be formed, which comprises portions subjected to energy irradiation and portions not subjected to energy irradiation, where the portions differ in terms of cell adhesiveness. Each step of this embodiment will be explained.

1. Step of Forming a Substrate for Pattern Formation

First, the step of forming a substrate for pattern formation in the present invention will be explained. The step of forming a substrate for pattern formation in the present invention is a step for forming such substrate that comprises a substrate and a cell adhesiveness variation material layer that is formed on the substrate and comprises a cell adhesiveness variation material whose cell adhesiveness is varied by the action of a photocatalyst along with energy irradiation.

This step can be carried out by applying a coating solution comprising a cell adhesiveness variation material to a substrate by a known application method such as a spin coating, a spray coating, a dip coating, a roll coating, or a bead coating method and thus forming a cell adhesiveness variation material layer. When a UV-hardened type component is contained as a binder, a photocatalyst-comprising layer can be formed through UV irradiation to carry out hardening treatment.

Such substrate and such cell adhesiveness variation material that can be used in this step are similar to those explained in the above section of the $1^{st}$ embodiment, "I. Cell array substrate."

2. Step of Forming a Cell Adhesiveness Variation Pattern

Next, the step of forming a cell adhesiveness variation pattern in this embodiment will be explained. The step of forming an adhesiveness variation pattern in this embodiment is a step for forming such pattern by arranging the above substrate for pattern formation and a photocatalyst-comprising-layer-side base plate that comprises a photocatalyst-comprising layer and a base body so that the above cell adhesiveness variation material layer and the above photocatalyst-comprising layer face each other, and then carrying out energy irradiation from a predetermined direction, so as to form a pattern wherein the cell adhesiveness of a cell adhesiveness variation material layer has been varied.

With this step wherein a photocatalyst-comprising layer in a photocatalyst-comprising-layer-side base plate and a cell adhesiveness variation material layer are arranged so that the layers face each other and energy irradiation is carried out in a desired pattern, the cell adhesiveness of regions (of a cell adhesiveness variation material layer) subjected to energy irradiation can be exclusively varied. Furthermore, a high-definition cell adhesiveness variation pattern can be formed, which comprises regions having good cell adhesiveness and regions having poor cell adhesiveness.

Such photocatalyst-comprising-layer-side base plate and energy irradiation that are used and carried out, respectively, in this step will be separately explained as follows.

(1) Photocatalyst-Comprising-Layer-Side Base Plate

First, a photocatalyst-comprising-layer-side base plate that is used in this embodiment will be explained.

Such photocatalyst-comprising-layer-side base plate that is used in this embodiment comprises at least a photocatalyst-comprising layer and a base body. Such base plate is generally prepared by forming a photocatalyst-comprising layer in the shape of thin film (formed by a predetermined method) on a base body. Furthermore, a photocatalyst-comprising-layer-side base plate that can also be used herein may comprise patterned photocatalyst-comprising-layer-side shielding portions or a primer layer formed thereon.

In this embodiment, at the time of energy irradiation, the above cell adhesiveness variation material layer and the photocatalyst-comprising layer in the above photocatalyst-comprising-layer-side base plate are arranged so that the layers face each other with a predetermined space between the two. The cell adhesiveness of the cell adhesiveness variation material layer is varied by the action of the photocatalyst-comprising layer of the photocatalyst-comprising-layer-side base plate. The photocatalyst-comprising-layer-side base plate is removed after energy irradiation, so that a cell adhesiveness variation pattern is formed. Each component of such photocatalyst-comprising-layer-side base plate will be explained.

a. Photocatalyst-comprising Layer

A photocatalyst-comprising layer that is used in this embodiment comprises at least a photocatalyst and may or may not comprise a binder. The photocatalyst-comprising layer is similar to the photocatalyst treatment layer described in the above $2^{nd}$ embodiment.

Figure 4:
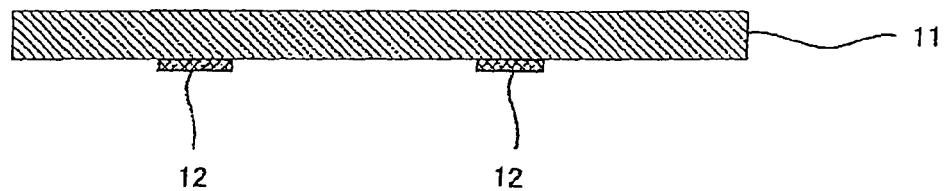
FIG. 4 is a schematic sectional view showing an example of the photocatalyst-comprising-layer-side base plate used in the present invention.

Such photocatalyst-comprising layer that is used in this embodiment may be, as shown in FIG. 3, for example, a layer formed on the whole surface of a base body 11. For example, as shown in FIG. 4, the photocatalyst-comprising layer may be a photocatalyst-comprising layer 12 patterned on the base body 11.

By patterning of such photocatalyst-comprising layer, patterned irradiation using a photomask or the like is not required at the time of energy irradiation. Furthermore, through irradiation of the whole surface, a cell adhesiveness variation pattern can be formed in a cell adhesiveness variation material layer.

A patterning method for such photocatalyst-comprising layer is not particularly limited. For example, such patterning can be carried out by a photolithography method or the like.

Furthermore, energy irradiation is carried out while closely contacting a photocatalyst-comprising layer and a cell adhesiveness variation material layer with each other. In such case, the properties of only portions where the photocatalyst-comprising layer has been actually formed are varied. Thus, such case is advantageous in that energy irradiation may be carried out from any direction, as long as portions where the above photocatalyst-comprising layer and cell adhesiveness variation material layer face each other are irradiated with energy. Another advantage is that energy to be used for irradiation is also not particularly limited to parallel energy such as parallel light.

b. Base Body

In this embodiment, as shown in FIG. 3, the photocatalyst-comprising-layer-side base plate 13 comprises at least a base body 11 and the photocatalyst-comprising layer 12 formed on the base body 11. At this time, the material composing a base body used herein is appropriately selected depending on the direction of energy irradiation described later, necessity for the transparency of the thus obtained cell array substrate, and the like.

Furthermore, such base body that is used in this embodiment may be a base body having flexibility, such as a film made of a resin, or a base body lacking flexibility, such as a glass substrate. Moreover, as another type of base body, an optical waveguide such as optical fiber can also be used. Such base body can be appropriately selected depending on the energy irradiation method.

In addition, to improve close contact between the surface of a base body and a photocatalyst-comprising layer, an anchor layer may also be formed on the base body. Examples of such anchor layer include a silane coupling agent and a titanium coupling agent.

c. Photocatalyst-Comprising-Layer-Side Shielding Portion

A photocatalyst-comprising-layer-side base plate that is used in this embodiment may comprise photocatalyst-comprising-layer-side shielding portions patterned thereon. With the use of such photocatalyst-comprising-layer-side base plate comprising the photocatalyst-comprising-layer-side shielding portions, it is not required to use a photomask or to carry out laser irradiation to draw a pattern at the time of energy irradiation. Furthermore, it is not required to carry out positioning for a photocatalyst-comprising-layer-side base plate and a photomask. Hence, a convenient step can be realized and no expensive apparatuses are needed for drawing irradiation. Thus, the use of such photocatalyst-comprising-layer-side base plate is advantageous in terms of cost.

The following two embodiments are possible for such photocatalyst-comprising-layer-side base plate comprising such photocatalyst-comprising-layer-side shielding portions, depending on the positions at which the photocatalyst-comprising-layer-side shielding portions are formed.

Figure 5:
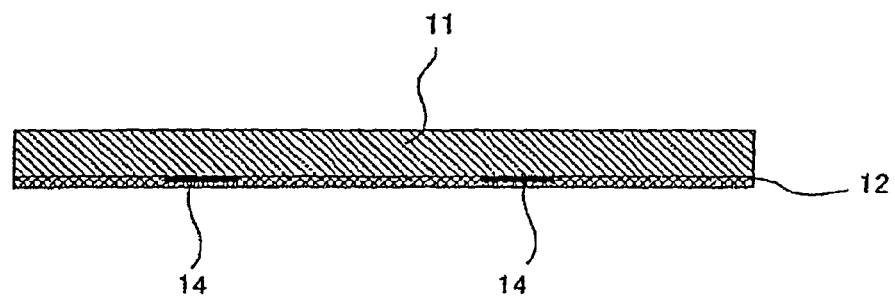
FIG. 5 is a schematic sectional view showing another example of the photocatalyst-comprising-layer-side base plate used in the present invention.
Figure 6:
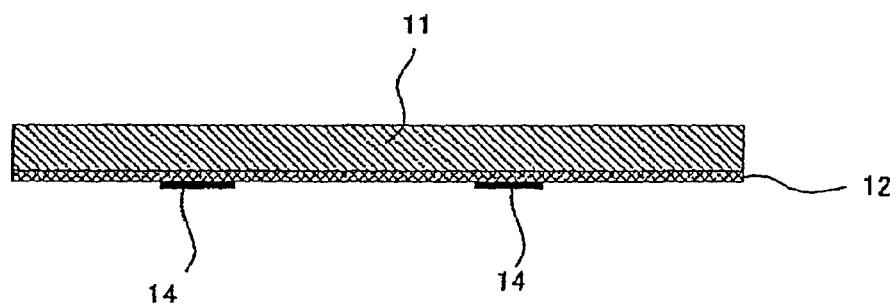
FIG. 6 is a schematic sectional view showing another example of the photocatalyst-comprising-layer-side base plate used in the present invention.

One embodiment of the photocatalyst-comprising-layer-side base plate is prepared as shown in FIG. 5, for example, wherein photocatalyst-comprising-layer-side shielding portions 14 are formed on the base body 11 and the photocatalyst-comprising layer 12 is formed on the photocatalyst-comprising-layer-side shielding portions 14. The other embodiment of the photocatalyst-comprising-layer-side base plate is prepared as shown in FIG. 6, for example, wherein the photocatalyst-comprising layer 12 is formed on the base body 11 and the photocatalyst-comprising-layer-side shielding portions 14 are formed on the photocatalyst-comprising layer 12.

In both embodiments, compared with the case of using a photomask, photocatalyst-comprising-layer-side shielding portions are arranged in the vicinity of portions where the above photocatalyst-comprising layer and cell adhesiveness variation material layer are to be arranged. Thus, the effect of energy scattering within a base body and the like can be reduced. Thus, it becomes possible to carry out patterned energy irradiation in an extremely precise manner.

Furthermore, in the above embodiment where photocatalyst-comprising-layer-side shielding portions are formed on a photocatalyst-comprising layer, when a photocatalyst-comprising layer and a cell adhesiveness variation material layer are arranged at predetermined positions, the film thickness of each photocatalyst-comprising-layer-side shielding portion is prepared to be the same as the width of the space between the two layers. Hence, the embodiment is advantageous in that the above photocatalyst-comprising-layer-side shielding portions can also be used as a spacer to maintain the above space at a constant width. Moreover, when the height of such portion as a spacer is insufficient, another spacer may be separately provided at the shielding portions.

Specifically, when the above photocatalyst-comprising layer and cell adhesiveness variation material layer are arranged so that the layers face each other with a predetermined space, the above photocatalyst-comprising-layer-side shielding portions and cell adhesiveness variation material layer can be arranged in close contact. This makes it possible to precisely obtain the above predetermined space. Furthermore, through energy irradiation from the photocatalyst-comprising-layer-side base plate under such state, it becomes possible to precisely form a cell adhesiveness variation pattern on the cell adhesiveness variation material layer.

A method for forming such photocatalyst-comprising-layer-side shielding portions is not particularly limited. Such method is appropriately selected and used depending on the properties of the surface on which photocatalyst-comprising-layer-side shielding portions are formed, shielding property as required against energy, and the like.

For example, such photocatalyst-comprising-layer-side shielding portions may be formed by forming a metal thin film made of chrome or the like with a thickness between approximately 1000 Å and 2000 Å by a sputtering method, a vacuum deposition method, or the like and then patterning the thin film. A general patterning method such as a sputtering method can be used as such patterning method.

Furthermore, such patterning method may also be a method that comprises preparing a layer that comprises shielding particles such as carbon fine particles, metallic oxide, an inorganic pigment, or an organic pigment in a resin binder and then patterning such layer. Examples of such resin binder that is used herein include 1 type of or a mixture of 2 or more types of resins such as a polyimide resin, an acrylic resin, an epoxy resin, polyacryl amide, polyvinyl alcohol, gelatin, casein, and cellulose, and a photosensitive resin. Furthermore, an O/W emulsion type resin composition such as an emulsified reactive silicone can be used. The thickness of each shielding portion made of resin can be determined within a range between 0.5 μm and 10 μm. As a patterning method used for such shielding portions made of resin, a generally employed method such as a photolithography method, printing method, or the like can be used.

Two possible positions of photocatalyst-comprising-layer-side shielding portions are explained in the above explanation. One of such position is between a base body and a photocatalyst-comprising layer. The other one is the surface of a photocatalyst-comprising layer. In addition to such positions, an embodiment that can also be employed comprises forming photocatalyst-comprising-layer-side shielding portions on the surface of a base body on the side where no photocatalyst-comprising layer is formed. In this embodiment, a photomask may be contacted closely but removably to such surface, for example. Such embodiment can be appropriately used for a case where a cell adhesiveness variation patterns is changed between small lots.

d. Primer Layer

Next, a primer layer that is used for a photocatalyst-comprising-layer-side base plate in this embodiment will be explained. In this embodiment, when photocatalyst-comprising-layer-side shielding portions are patterned on a base body as described above and then a photocatalyst-comprising layer is formed thereon, so as to prepare a photocatalyst-comprising-layer-side base plate, a primer layer may be formed between the above photocatalyst-comprising-layer-side shielding portions and photocatalyst-comprising layer.

The action and functions of such primer layer are not always clear. Through the formation of the primer layer between photocatalyst-comprising-layer-side shielding portions and a photocatalyst-comprising layer, it is thought that the primer layer exhibits a function to prevent the diffusion of impurities (that are factors that inhibit variation in cell adhesiveness of a cell adhesiveness variation material layer caused by the action of a photocatalyst) coming from inside of the photocatalyst-comprising-layer-side shielding portions or each opening existing between the photocatalyst-comprising-layer-side shielding portions. Particular examples of such impurities include residues and impurities such as metal and metal ions that are generated at the time of patterning of the photocatalyst-comprising-layer-side shielding portions. Therefore, by the formation of such primer layer, treatment for causing variation in cell adhesiveness can proceed with high sensitivity. As a result, it becomes possible to obtain a pattern with high resolution.

In addition, such primer layer in this embodiment prevents impurities (existing not only on the photocatalyst-comprising-layer-side shielding portions but also at an opening formed between such photocatalyst-comprising-layer-side shielding portions) from affecting the action of a photocatalyst. The primer layer is preferably formed on the whole surface of the photocatalyst-comprising-layer-side shielding portions including the opening.

Such primer layer in this embodiment is not particularly limited, as long as it is formed such that photocatalyst-comprising-layer-side shielding portions of a photocatalyst-comprising-layer-side base plate and a photocatalyst-comprising layer do not contact with each other.

A material composing such primer layer is not particularly limited. An inorganic material hardly decomposed by the action of a photocatalyst is preferred. A specific example of such material is amorphous silica. When such amorphous silica is used, a precursor of such amorphous silica is a silicon compound represented by general formula $SiX_4$, where X indicates halogen, a methoxy group, an ethoxy group, an acetyl group, or the like. Hydrolysates of such compound, such as silanol or polysiloxane with an average molecular weight of 3000 or less, are preferable.

Furthermore, the film thickness of such primer layer is preferably within the range between 0.001 μm and 1 μm and particularly preferably within the range between 0.001 μm and 0.1 μm.

(2) Energy Irradiation

Next, energy irradiation in this step will be explained. In this embodiment, the above cell adhesiveness variation material layer and the above photocatalyst-comprising layer of the above photocatalyst-comprising-layer-side base plate are arranged so that the layers face each other, and then energy irradiation is carried out from a predetermined direction. Thus, a pattern with variation in cell adhesiveness of the cell adhesiveness variation material layer can be formed.

The above expression "are arranged" means a state where the layers are arranged so that a photocatalyst substantially acts on the surface of the cell adhesiveness variation material layer. The term also means, in addition to a state where the layers are caused to come into actual and physical contact, a state where the above photocatalyst-comprising layer and the above cell adhesiveness variation material layer are arranged with a predetermined space. Such space is preferably 200 μm or less.

The above space in this embodiment is particularly within the range between 0.2 μm and 10 μm and preferably within the range between 1 μm and 5 μm in consideration of extremely good patterning accuracy, high photocatalyst sensitivity, and good efficiency of causing variation in the cell adhesiveness of a cell adhesiveness variation material layer. The space within such range is particularly effective for a cell adhesiveness variation material layer with a small area that enables control of such space with particularly high accuracy.

On the other hand, when a cell adhesiveness variation material layer with an area that is as large as 300 mm×300 mm or greater, for example, is treated, it is extremely difficult to form a fine space as described above between a photocatalyst-comprising-layer-side base plate and a cell adhesiveness variation material layer without causing them to come into contact. Therefore, when a cell adhesiveness variation material layer has relatively a large area, the above space is preferably within a range between 10 μm and 100 μm and particularly preferably within the range between 10 μm and 20 μm. The space set to be within such range can have effects of: causing no problems such as lowered patterning accuracy (e.g., a blur patterning), deteriorated photocatalyst sensitivity, and lower efficiency of causing variation in cell adhesiveness as a result of such deteriorated sensitivity; and not generating uneven variation in the cell adhesiveness on a cell adhesiveness variation material layer.

When such cell adhesiveness variation material layer with a relatively large area is subjected to energy irradiation, within an apparatus for energy irradiation, the space between a photocatalyst-comprising-layer-side base plate and a cell adhesiveness variation material layer is preferably set in an apparatus for positioning the plate and the layer within the range between 10 μm and 200 μm and particularly preferably within the range between 10 μm and 20 μm. Determination of the space within such a range makes it possible to arrange a photocatalyst-comprising-layer-side base plate and a cell adhesiveness variation material layer without causing any drastic decrease in patterning accuracy or in photocatalyst sensitivity, and without the two coming into contact.

A photocatalyst-comprising layer and the surface of a cell adhesiveness variation material layer are arranged with a predetermined space as described above. Thus, removal of active oxygen species generated by the action of oxygen, water, and a photocatalyst is facilitated. Specifically, when the space between a photocatalyst-comprising layer and a cell adhesiveness variation material layer is narrower than those within the above ranges, it becomes difficult to remove the above active oxygen species. As a result, the rate of causing variation in cell adhesiveness may be lowered. Thus, such narrow space is not preferable. Furthermore, arrangement with a space wider than those within the above ranges makes it difficult for the generated active oxygen species to reach the cell adhesiveness variation material layer. This case is also not preferable because this may result in a lower rate of causing variation in cell adhesiveness.

An example of a method for arranging a photocatalyst-comprising layer and a cell adhesiveness variation material layer with uniform and extremely narrow space is a method that uses a spacer. A uniform space can be formed with the use of a spacer. Furthermore, portions (of the surface of a cell adhesiveness variation material layer) to which the spacer is caused to come into contact are free from the action of a photocatalyst. Hence, the spacer is prepared to have a pattern similar to that of the above cell adhesiveness variation pattern, so that a predetermined cell adhesiveness variation pattern can be formed on a cell adhesiveness variation material layer.

In this embodiment, such arrangement should be maintained at least during energy irradiation.

Types of energy to be used for irradiation, irradiation method, the amount of energy irradiation, and the like are similar to those explained in the above $1^{st}$ embodiment.

In addition, the present invention is not limited to the above embodiments. The above embodiments are provided for illustrative purposes. Any embodiment that has substantially the same constitution as that of the technical idea disclosed in the claims of the present invention and exerts action and effects similar to those exerted by the present invention is encompassed within the technical scope of the present invention.

III. Adhesion of Angiogenic Cells to Cell Array Substrate

In the cell array substrate, angiogenic cells are caused to adhere to the regions having good cell adhesiveness of the above cell array substrate having a cell adhesiveness variation pattern that comprises regions having different cell adhesiveness. The cell array substrate of the present invention has such cell adhesiveness variation pattern that comprises regions having good cell adhesiveness and regions having inhibited cell adhesiveness, as described above. Hence, when cells are uniformly inoculated on the surface of the cell array substrate and then subjected to incubation for a predetermined time, the thus obtained cell array substrate has a cell pattern formed to comprise regions having good cell adhesiveness, to which the cells adhere, and regions having inhibited cell adhesiveness, to which no cells adhere. At such time, the substrate is subjected to liquid cleaning after incubation, so that the cells that weakly adhere to the substrate can be removed and a clearer cell pattern can be obtained.

A culture sample containing angiogenic cells is preferably previously subjected to diffusion treatment by which a biological tissue is finely fragmented and diffused in a liquid, or it is subjected to separation treatment by which cells other than the target cells and other substances inhibiting the relevant experiment in a biological tissue are removed.

Prior to inoculation of cells on the cell array substrate, it is preferable to increase the number of the target cells through preliminary culture of the cells contained in a culture sample by any one of a variety of culture methods. Examples of a general method that can be employed for such preliminary culture include a monolayer culture method, a coated dish culture method, and a gel culture method. Regarding preliminary culture, as a culture method that comprises causing cells to adhere to the surface of a support and then culturing the cells, the monolayer culture method is already known. Specifically, for example, when a culture sample and a culture solution are placed in a culture container and then maintained under certain environmental conditions, specific viable cells alone will grow while adhering to the surface of a support such as the culture container. The apparatuses, treatment conditions, and the like to be used herein are employed according to the general monolayer culture method and the like. As a material employed for the surface of a support to which cells adhere and grow, a material with which cell adhesion and cell growth can be successfully carried out is selected. Furthermore, a chemical substance (namely, a cell adhesion factor) with which cell adhesion and cell growth can be successfully carried out is previously applied to the surface of a support.

After culture, the culture solution within the culture container is removed, thereby removing unnecessary components that do not adhere to the surface of the support in the culture sample. Hence, only the viable cells adhering to the surface of the support can be harvested. Means such as EGTA-trypsinization can be applied for harvesting viable cells adhering to the surface of the support.

The above preliminarily cultured cells are inoculated on the cell array substrate in a culture solution. A method for cell inoculation and an inoculation amount are not particularly limited. For example, a method disclosed in "Tissue Culture Technology (*Soshiki Baiyo no Gijutu*)" (edited by The Japanese Tissue Culture Association, pp. 266 to 270, issued by Asakura Pub. Co., 1999) can be used. It is preferable to inoculate cells in a sufficient amount so that the cells are not required to grow on the cell array substrate and so that the cells adhere to the substrate in the form of monolayer. This is because tissue formation by cells is inhibited when cells aggregate, and even when cells are transferred to and then cultured on a basal membrane layer, their functions will be impaired. Specifically, approximately $2 \times 10^5$ cells are inoculated per 400 mm$^2$.

It is preferable to cause cells to adhere to regions having good cell adhesiveness through incubation of the cells that have been inoculated on a cell array substrate in a culture solution. As a culture solution, a medium that is generally used in the technical field can be used. According to the cell types to be used herein, a basic medium disclosed in "Tissue Culture Technology (*Soshiki Baiyo no Gijutu*)" (edited by The Japanese Tissue Culture Association, issued by Asakura Pub. Co., 3rd ed., p. 581) can be used. Examples of such medium include an MEM medium, a BME medium, a DME medium, an AMEM medium, an IMEM medium, an ES medium, a DM-160 medium, Fisher medium, an F12 medium, a WE medium, and an RPMI medium. Furthermore, one of these media supplemented with a serum component (e.g., fetal calf serum) or the like, a commercial serum free medium, and the like can be used.

Time for incubation is generally between 30 minutes and 48 hours and preferably between 4 hours and 24 hours. When cells are incubated for a proper time period and then the substrate is washed, cells adhere to regions of the cell array substrate having good cell adhesiveness but do not adhere to regions of the cell array substrate having inhibited cell adhesiveness. Also, it becomes possible to easily transfer the remaining cells to a basal membrane layer.

The temperature for incubation differs depending on the types of cells to be caused to adhere, and it is generally 37° C. Cells are preferably incubated under a $CO_2$ atmosphere using a $CO_2$ cell culture incubator. After incubation, the cell array substrate is washed, so as to wash off cells that have not adhered to the substrate. Thus, the cells can be arrayed in a pattern.

Figure 7:
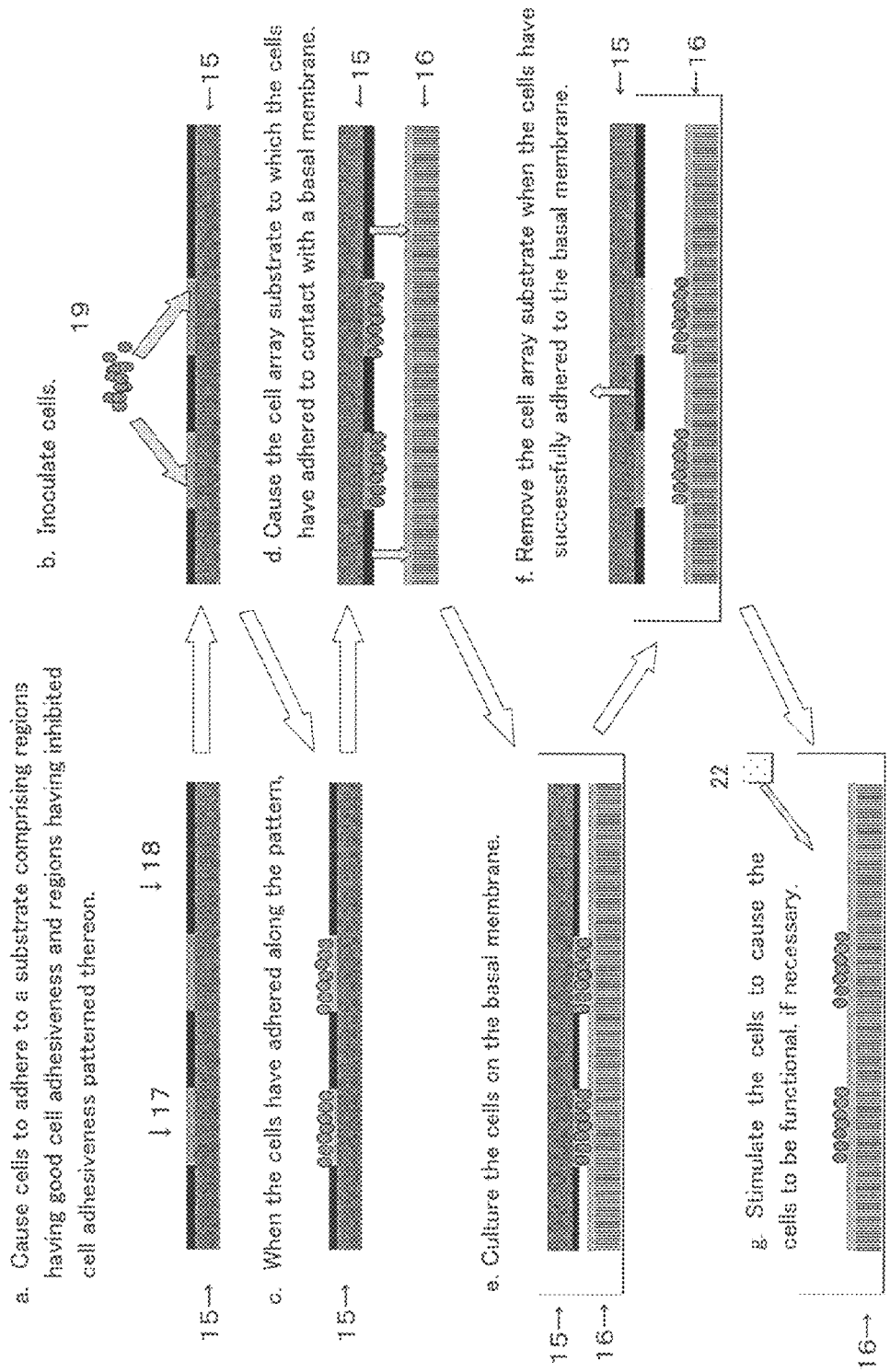
FIG. 7 shows an embodiment of a step for causing angiogenic cells to adhere to a cell array substrate in a pattern and transferring the adhered angiogenic cells to the basal membrane layer.

FIG. 7 shows an embodiment of the step of causing angiogenic cells to adhere to a cell array substrate in a pattern and then transferring the adhered cells to a basal membrane layer. Angiogenic cells are inoculated on a cell array substrate (15) comprising regions having good cell adhesiveness (17) and regions having inhibited cell adhesiveness (18) patterned thereon. The cells are then caused to adhere to form a pattern. Subsequently, the cell array substrate to which the angiogenic cells adhere is caused to come into close contact with a basal membrane layer that is provided covering almost the entire surface of a region of a tissue-forming cell layer on which a blood vessel network will be formed, so as to transfer and culture the cells. If necessary, the cells are stimulated with a cell stimulating factor (22). In addition, as shown in the figure, the basal membrane layer is not necessarily formed covering the entire surface of the tissue-forming cell layer, and it may be formed covering a region to which a blood vessel network will be transferred.

BEST MODE FOR CARRYING OUT THE INVENTION

Hereinafter, the present invention will be described in detail by referring to examples, but the present invention is not limited by these examples.

Example 1

Preparation a Cell Array Substrate 1.5 g of fluoroalkyl silane TSL8233 (GE Toshiba Silicones), 5.0 g of tetramethoxysilane TSL8114 (GE Toshiba Silicones), and 2.4 g of $5.0\times10^{-3}$N HCl were mixed for 12 hours and then diluted 10-fold with isopropyl alcohol.

Next, 2.0 g of the solution was applied to a 10 cm×10 cm soda glass substrate using a spin coater at 1000 rpm for 5 seconds. The substrate was dried at 150° C. for 10 minutes.

Next, 3.0 g a titanium oxide sol solution (ISHIHARA SANGYO KAISHA, LTD. STK-03) diluted 3-fold with isopropyl alcohol was used as a composition for a photocatalyst-comprising layer.

The above composition for a photocatalyst-comprising layer was applied to the patterned surface (on which line portions each having a width of 60 μm and space portions each having a width of 400 μm had been arranged alternately) of a line & space negative photomask (quartz) using a spin coater at 700 rpm for 3 seconds, followed by 10 minutes of drying treatment at 150° C. Thus, a photomask comprising a transparent photocatalyst-comprising layer was formed.

The above photocatalyst-comprising layer surface of the photomask and the above cell adhesiveness variation material layer surface of the substrate were arranged with a space of 10 μm between the surfaces. UV exposure was carried out from the photomask side using a mercury lamp (wavelength: 365 nm) with an illuminance of 25.0 mW/cm² for a predetermined time. The thus obtained cell array substrate had a cell adhesiveness variation pattern wherein linear regions having good cell adhesiveness and each having a width of 60 μm and the spaces comprising regions having inhibited cell adhesiveness and each having a width of 400 μm had been arranged alternately.

Example 2

Culture and Adhesion of Vascular Endothelial Cells onto the Cell Array Substrate As cells to be cultured, bovine carotid-derived vascular endothelial cells (Onodera M, Morita I, Mano Y, Murota S: Differential Effects of Nitric Oxide on the Activity of Prostaglandin Endoperoxide h Synthase-1 and -2 in Vascular Endothelial Cells, Prostag Leukotress 62: 161-167, 2000) of 5th to 20th generations obtained by successive culture were used.

Bovine carotid-derived vascular endothelial cells that had reached confluence in a 10 cm dish were removed by 0.05% trypsin-EDTA treatment. The number of cells was counted using a Coulter Counter™ ZM and then the concentration was adjusted to $10^6$ cells/ml. The cell array substrate (exposure time: 360 seconds) prepared in Example 1 was sterilized with an autoclave. The cell array substrate was placed on the culture dish (Heraeus Quadriprem™, 76 mm×26 mm, and 1976 mm²) containing a culture solution (MEM medium comprising 5% fetal calf serum) and then the above endothelial cells were inoculated at $10^6$ cells/5 ml per well. The cells were incubated for 24 hours using a $CO^2$ incubator.

A carbocyanine fluorescent dye (DiI, Invitrogen Corp.) was dissolved in an MEM medium comprising 5% fetal calf serum at a concentration of 10 μg/ml. The above cell array substrate on which the cells had been arrayed was immersed in the medium, followed by 1 hour of culture at 37° C. Subsequently, the cell array substrate was returned in an MEM medium comprising 5% fetal calf serum.

Example 3 i) Mouse hepatic parenchymal cells were harvested and then cultured on a commercial 96-well NIPAAm (poly-N-isopropylacrylamide) plate. After staining with a carbocyanine fluorescent dye (DiO, Invitrogen Corp.) with the above concentration, the medium containing the dye was replaced with an MEM medium comprising 5% fetal calf serum.

GFR Matrigel (Becton, Dickinson and Company) was diluted 10-fold with an MEM medium comprising 5% fetal calf serum. The medium containing the gel was added at 25 μl per well of the plate where mouse hepatic parenchymal cells had been cultured, followed by 1 hour of culture at 37° C. Thus, a basal membrane layer comprising a gel thin film layer was formed on the cells.

ii) The substrate prepared in Example 2, on which vascular endothelial cells had been arrayed, was immersed in the hepatic-parenchymal-cell-cultured plate prepared in i), so as to cause the basal membrane layer on the hepatic parenchymal cells to come into contact with vascular endothelial cells. The cells were cultured at 37° C. for 24 hours and then the cell array substrate was removed (separated).

iii) The plate was shaken at approximately 20° C. for 30 minutes, light pipetting was carried out, and then the thus formed tissue construct was removed using forceps.

iv) An immunodeficient mouse was anesthetized, the dorsal region was incised, and the tissue construct prepared through i) to iii) was transplanted into the mouse liver. The transplanted site was sutured. On day 1 and day 3 after suturing, the transplanted site was incised again, and then the transplanted tissue was observed under a confocal laser microscope (DiI→excitation wavelength of 530 nm/observance wavelength of 590 nm and DiO→excitation wavelength of 480 nm/observance wavelength of 510 nm).

Results

The growth of the transplanted hepatic parenchymal cells was confirmed by observation at an excitation wavelength of 480 nm. Furthermore, transplanted vascular endothelial cells were observed at an excitation wavelength of 530 nm. Thus, it was confirmed that capillary vessels had been formed in the same pattern as the previously formed pattern of vascular endothelial cells.

Example 4

Vascular endothelial cells were arrayed on a cell array substrate according to procedures similar to those used in Examples 1 and 2. Furthermore, the steps i) to iii) of Example 3 were carried out, and tissue constructs each comprising hepatic parenchymal cells, a basal membrane, and blood vessels were prepared.

Next, 3, 5, and 7 pieces of the tissue constructs thus prepared were laminated together, so as to prepare laminated tissue constructs. Immediately after lamination, the tissue constructs were each transplanted into the livers of immunodeficient mice. Each transplanted site was sutured. On day 1 and day 3 after suturing, each transplanted site was incised again and then the transplanted tissue was observed.

Results

The growth of the transplanted hepatic parenchymal cells was confirmed by observation at an excitation wavelength of 480 nm. Furthermore, transplanted vascular endothelial cells were observed at an excitation wavelength of 530 nm. Thus, it was confirmed that capillary vessels had been formed in the same pattern as the previously formed pattern of the vascular endothelial cells. The amounts of hemoglobin in the excised tissues were analyzed. As a result, it was confirmed that the amount of hemoglobin in each transplanted site was equivalent to that in non-transplanted sites of the mouse liver.

Comparative Example 4

Tissue constructs each comprising hepatic parenchymal cells and a basal membrane layer were formed according to the steps i) to iii) of Example 3. Next, 3, 5, and 7 pieces of the tissue constructs thus prepared were laminated together, so as to form laminated tissue constructs. Immediately after lamination, the laminated tissue constructs were each transplanted into the livers of immunodeficient mice. The transplanted sites were sutured. On day 1 and day 3 after suturing, each transplanted site was incised again and then the transplanted tissue was observed.
Results In the cases where 5 or 7 pieces of tissue constructs had been laminated together, the necrosis of the transplanted hepatic parenchymal cells was observed at an excitation wavelength of 480 nm. Furthermore, the amounts of hemoglobin in the excised tissues were analyzed. As a result, almost no hemoglobin was observed at the transplanted sites.

Example 5

Vascular endothelial cells were arrayed on a cell array substrate according to procedures similar to those used in Examples 1 and 2. Furthermore, the steps i) to iii) of Example 3 were carried out, so as to form $1^{st}$ tissue constructs each comprising hepatic parenchymal cells, a basal membrane, and blood vessels. Next, $2^{nd}$ tissue constructs each comprising hepatic parenchymal cells and a basal membrane layer were formed according to the steps i) and iii) of Example 3.

3 pieces of the thus formed $1^{st}$ tissue constructs and 3 pieces of the thus formed $2^{nd}$ tissue constructs (total 6 tissue constructs) were laminated together alternately, so as to form laminated tissue constructs. Immediately after lamination, the laminated tissue constructs were each transplanted to the livers of immunodeficient mice, and then the transplanted sites were sutured. On day 1 and day 3 after suturing, each transplanted site was incised again, and then the transplanted tissue was observed.

The growth of the transplanted hepatic parenchymal cells was confirmed by observation at an excitation wavelength of 480 nm. Furthermore, transplanted vascular endothelial cells were observed at an excitation wavelength of 530 nm. Thus, it was confirmed that capillary vessels had been formed in the same pattern as the previously formed pattern of the vascular endothelial cells. The amounts of hemoglobin in the excised tissues were analyzed. As a result, it was confirmed that the amount of hemoglobin in each transplanted site was half or more of the amount resulting in Example 4.

All publications, patents, and patent applications cited herein are incorporated herein by reference in their entirety.

INDUSTRIAL APPLICABILITY

According to the present invention, an artificial tissue construct that has means for transporting nutrients, oxygen, waste products, or the like and is viable in vivo can be provided.

The invention claimed is:

1. A tissue construct formed in vitro, which comprises a vascular layer, a basal membrane layer, and a tissue-forming cell layer,
    wherein the basal membrane layer comprises an extracellular matrix from a source other than the vascular layer, and
    wherein the vascular layer consists of blood vessel tissue comprising angiogenic cells that are seeded in a linear, mesh, circular, or quadrille pattern on the basal membrane layer.

2. The tissue construct according to claim 1, wherein the basal membrane layer is present on the tissue-forming cell layer and the vascular layer is present on the basal membrane layer.

3. A method for regenerating a tissue, which comprises transplanting the tissue construct according to claim 1.

4. A laminated tissue construct formed in vitro, comprising at least one layer of each of vascular layers, basal membrane layers, and tissue-forming cell layers, wherein all of the layers are laminated together,
    wherein the basal membrane layers comprise an extracellular matrix from a source other than the vascular layers, and
    wherein each of said vascular layer comprises angiogenic cells arrayed in a linear, mesh, circular, or quadrille pattern, and
    wherein a first basal membrane layer is present on a first tissue-forming cell layer, a first vascular layer is present on the first basal membrane layer, and the first tissue-forming cell layer is present on a second basal membrane layer or a second vascular layer.

5. A method for regenerating a tissue, which comprises transplanting the tissue construct according to claim 4.

6. A tissue construct comprising a vascular layer, a basal membrane layer, and a tissue-forming cell layer, wherein the basal membrane layer is formed covering almost the entire surface of a region of the tissue-forming cell layer on which the vascular layer is formed,
    wherein the basal membrane layer comprises an extracellular matrix from a source other than the vascular layer, and
    wherein said vascular layer consists of blood vessel tissue comprising angiogenic cells that are seeded in a linear, mesh, circular, or quadrille pattern on the basal membrane layer.

7. A laminated tissue construct, comprising at least one layer of each of vascular layers, basal membrane layers, and tissue-forming cell layers, wherein a basal membrane layer is formed covering almost the entire surface of a region of a tissue-forming cell layer on which the vascular layer is formed,
    wherein the basal membrane layer comprises an extracellular matrix from a source other than the vascular layer, and
    wherein each of said vascular layers comprises angiogenic cells arrayed in a linear, mesh, circular, or quadrille pattern, and
    wherein a first basal membrane layer is present on a first tissue-forming cell layer, a first vascular layer is present on the first basal membrane layer, and the first tissue-forming cell layer is present on a second basal membrane layer or a second vascular layer.

* * * * *